United States Patent [19]

Bindra et al.

[11] 4,365,077

[45] Dec. 21, 1982

[54] 11-DESOXY-16-ARYLOXY-ω-TETRANOR-PROSTAGLANDINS

[75] Inventors: Jasjit S. Bindra, Groton; James F. Eggler, Stonington; Michael R. Johnson, Gales Ferry; Thomas K. Schaaf, Old Lyme, all of Conn.

[73] Assignee: Pfizer Inc., New York, N.Y.

[21] Appl. No.: 13,899

[22] Filed: Feb. 22, 1979

Related U.S. Application Data

[62] Division of Ser. No. 589,386, Jun. 23, 1975, abandoned.

[51] Int. Cl.³ ............................................ C07C 177/00
[52] U.S. Cl. ........................................ 560/53; 560/64; 560/65; 560/56; 562/464; 562/471; 562/462
[58] Field of Search ...................... 560/53, 64, 65, 56; 562/464, 471, 462

[56] References Cited

U.S. PATENT DOCUMENTS 3,984,400  5/1976  Eggler et al. ........................ 560/53

OTHER PUBLICATIONS

Derwent Abstract 59715x/32, 01/07/76, BE 839.533, (14.03.75).

*Primary Examiner*—Paul J. Killos
*Attorney, Agent, or Firm*—Connolly and Hutz

[57] ABSTRACT

11-Desoxy-16-aryloxy-ω-tetranorprostaglandins are disclosed. The novel prostaglandins of this invention have been found to have activity profiles comparable to the parent prostaglandins but they exhibit a greater tissue specificity of action.

12 Claims, No Drawings

11-DESOXY-16-ARYLOXY-ω-TETRANORPROSTA-GLANDINS

CROSS-REFERENCE TO RELATED APPLICATION

This application is a division of application Ser. No. 589,386 filed June 23, 1975, abandoned.

BACKGROUND OF THE INVENTION

This invention relates to certain novel analogs of the naturally occurring prostaglandins. In particular, it relates to novel 11-desoxy-16-aryloxy-ω-tetranorprostaglandins and various novel intermediates useful in their preparation.

The prostaglandins are C-20 unsaturated fatty acids which exhibit diverse physiological effects. Each of the known, naturally occurring prostaglandins is derived from prostanoic acid which has the structure and position numbering:

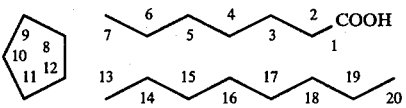

[Bergstrom et al., *Pharmacol. Rev.* 20, 1 (1968), and references cited therein.] A systematic name for prostanoic acid is 7-[(2β-octyl)-cyclopent-1α-yl]heptanoic acid.

PGA$_2$ has the structure:

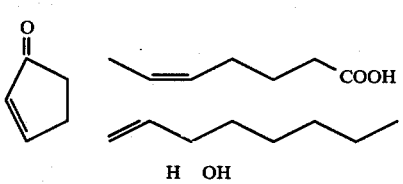

PGB$_2$ has the structure:

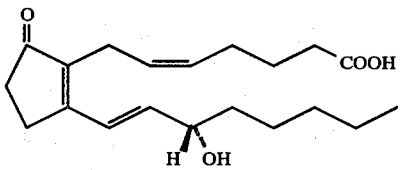

PGE$_2$ has the structure:

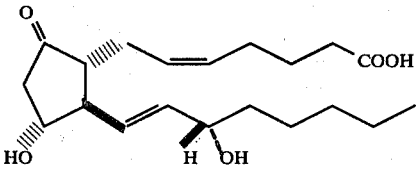

PGF$_{2\alpha}$ has the structure:

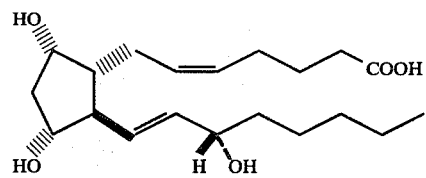

PGF$_{2\beta}$ has the structure:

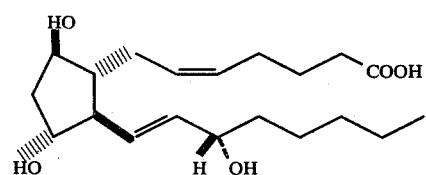

Each of the PG$_1$ prostaglandins, PGE$_1$, PGF$_{1\alpha}$, PGF$_{1\beta}$, PGA$_1$, and PGB$_2$, has a structure the same as the corresponding PG$_2$ compound except that the cis double bond between C-5 and C-6 is replaced by a single bond. For example, PGA$_1$ has the structure:

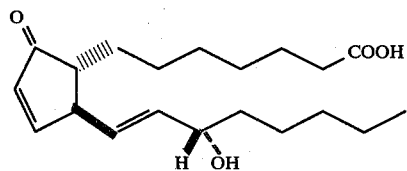

The PG$_0$ compounds are those in which there are no double bonds in either side chain. For instance, PGE$_0$ has the structure

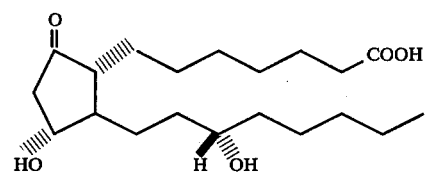

Broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C-15 in the above formulas is in S configuration. [See, *Nature*, 212, 38 (1966) for discussion of the stereochemistry of the prostaglandins.]

Molecules of the known prostaglandins each have several centers of asymmetry, and can exist in racemic (optically inactive) form and in either of the two enantiomeric (optically active) forms, i.e. the dextrorotatory and levorotatory forms. As drawn above, each structure represents the particular optically active form of the prostaglandin which is obtained from certain mammalian tissues, for example, sheep vesicular glands, swine lung, or human seminal plasma, or by carbonyl and/or double bond reduction of that prostaglandin. [Bergstrom et al., cited above.] The mirror image or optical antipode of each of the above structures represents the other enantiomer of that prostaglandin.

For instance, the optical antipode or PGF$_{2\alpha}$ (ent-PGF$_{2\alpha}$) is drawn as

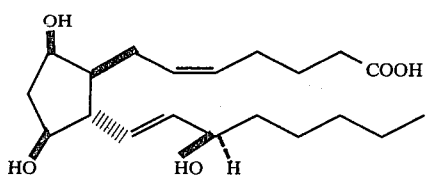

The racemic form of a prostaglandin contains equal numbers of a particular stereoisomer and its mirror image. When reference to a prostaglandin racemate is intended, the symbols "rac" or "dl" will precede in prostaglandin name. Two structures are needed to represent a racemate. For instance, the structure of dl-PGF$_{2\alpha}$ is properly represented as an equimolar mixture of PGF$_{2\alpha}$ and ent-PGF$_{2\alpha}$. The terms PGE$_1$, PGE$_2$, PGF$_{1\alpha}$ and the like as used herein will mean that stereoisomer with the same absolute configuration as the corresponding prostaglandin found in mammalian tissue.

In an optical antipode, the absolute configuration at all of the above-mentioned centers of asymmetry is inverted. In an epimer, the configuration is inverted at one or more but not all of the centers. For instance, the absolute configuration of the 15-hydroxy group in 15-epi-PGF$_{2\alpha}$ is the R configuration and is shown as

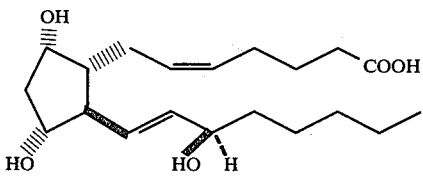

It will be noted that only the configuration at the 15-position is inverted and that at the other centers of asymmetry, namely the 8-, 9-, 11- and 12-positions, the absolute configuration is the same as that in the naturally-occurring mammalian PGF$_{2\alpha}$. Racemic mixtures of epimers may also exist for instance, if 15-keto-PGF$_{2\alpha}$ is reduced with zinc borohydride or a hindered alkyl borohydride, the resulting product is a racemic mixture of 15α-hydroxy and 16β-hydroxy-PGF$_{2\alpha}$.

PGE$_1$, PGE$_2$, and the corresponding PGF$_\alpha$, PGF$_\beta$, PGA, and PGB compounds, and many of their derivatives such as the esters, acylates, and pharmacologically acceptable salts, are extremely potent inducers of various biological responses. These compounds are, therefore, potentially useful for pharmacological purposes. [Bergstrom et al., cited above.] A few of those biological responses are systemic arterial blood pressure lowering in the case of the PGF$_\beta$, PGE and PGA compounds as shown in cardiac cannulated rats or dogs; pressor activity for the PGF$_\alpha$ compounds; stimulation of smooth muscle as shown by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury; in the case of the PGE and PGB compounds, stimulation of epidermal proliferation and keratinization as shown when applied in culture to embryonic chick and rat skin segments; and in the case of PGF$_2$ and PGE compounds luteolytic activity as shown in hamsters and rats.

Prostaglandins are useful to prevent, control, or alleviate a wide variety of diseases and undesirable physiological conditions in avians and mammals, including humans, useful domestic animals, pets, and zoological specimens, and in laboratory animals, for example, mice, rats, rabbits, and monkeys.

For example, these compounds, especially those of the E series, are useful in mammals, including man, as bronchodilators [Cuthbert, Brit. Med. J., 4: 723–726, 1969]. As nasal decongestants, the compounds are used in a dose range of about 10 μg. to about 10 mg. per ml. of a pharmacologically suitable liquid vehicle or as an aerosol spray, both for topical application.

The PGE compounds are useful in the treatment of asthma because of their activity as bronchodilators and-/or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of routes in a number of dosage forms, e.g., orally in the form of tablets, capsules, or liquids; rectally in the form of suppositories; parenterally with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day. These prostaglandins can also be combined advantageously with other anti-asthmatic agents, such as sympathomimetics (isoproterenol, phenylephrine, epherine, etc.); xanthine derivatives (theophylline and aminophyllin); and corticosteroids (ACTH and prednisolone). Regarding use of these compounds see south African Pat. No. 68/1055.

The PGE and PGA compounds are useful in mammals, including man and animals to reduce and control excessive gastric secretion, thereby reducing or avoiding gastrointestinal ulcer formation, and accelerating the healing of such ulcers already present in the gastrointestinal tract. [Shaw and Ramwell, In: *Worchester Symposium on Prostaglandins,* Wiley (New York, 1968), pp. 55–64.] For this purpose, the compounds are administered parenterally by injection or intravenous infusion in an infusion does range of about 0.1 μg. to about 500 μg. per kg. of body weight per minute, or in a total daily dose by injection or infusion in the range of about 0.1 to about 20 mg. per kg. of body weight per day.

The PGE compounds are useful whenever it is desired to inhibit platelet aggregation, to reduce the adhesive character of platelets, and to move or prevent the formation of thrombi in mammals, including man, rabbits, or rats. [Emmons et al., *Brit. Med. J.,* 2: 468–472, 1967.] These compounds are, for example, useful in the treatment and prevention of mycardial infacts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically. For rapid response, especially in emergency situation, the intraveneous route of administration is preferred. Doses in the range of about 0.005 to about 20 mg. per kg. of body weight per day are used.

The PGE compounds are especially useful in additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to the new body. Under such conditions, aggregated platelets tend to block the blood vessels and portions of the circulation apparatus. Such aggregation is inhibited by the presence of a prostaglandin. For this purpose, the compound is added gradually or in single or multiple portions to be circulating blood, to the blood of the donor animal, to the perfused body portion, attached or detached, to the recipient, or to two or all of those at a total steady state dose of about 0.001 to 10 mg. per liter or circulating fluid.

PGE and $PGF_2$ compounds are extremely potent in causing stimulation of smooth muscle, and are also highly active in potentiating other known smooth muscle stimulators. Therefore, $PGE_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puperperium. For the latter purpose, the PGE compound is administered intravenously immediately after abortion or delivery at a dose in the range of about 0.01 to about 50 µg, per kg. of body weight per minute until the desired effect is obtained. Subsequent doses are given parenterally during puerperium in the range 0.01 to 2 mg. per kg. of body weight per day.

The PGE, PGA and $PGF_\beta$ compounds are useful as hypotensive agents and vasodilators [Bergstrom et al., *Acta Physiol. Scand.*, 64: 332-333, 1965; *Life Sci.*, 6:449-455, 1967] in mammals, including man. To lower systemic arterial blood pressure, the compounds are administered by intravenous infusion at the rate of about 0.01 to about 50 µg. per kg. of body weight per minute, or in single or multiple doses of about 25 to 500 µg. per kg. of body weight total per day. [Weeks and King, *Federation Proc.* 23:327, 1964; Bergstrom, et al., 1965, op. cit.; Carlson, et al., *Acta Med. Scand.* 183:423-430, 1968; and Carlson et al., *Acta Physiol. Scand.* 75:161-169, 1969.]

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephretic states, the vasopressin action of these compounds is especially useful. Illustratively, the PGA compounds are useful in alleviating and correcting cases of edema resulting from massive surface burns, in the management of shock, etc. For these purposes, the PGA compounds are preferably firt administered by intravenous injection at a dose in the range 10 to 1000 µg. per kg. of body weight or by intravenous infusion at a dose in the range 0.1 to 20 µg. per kg. of body weight per minute until the desired effect is obtained. Subsequent doses are given by intravenous, intramuscular, or subcutaneous injection or infusion in the range 0.05 to 2 mg. per kg. of body weight per day.

The PGE compounds, especially $PGE_1$, are useful in the treatment of psoriasis (Fiboh, et. al., *Nature*, 254, 351 (1975)). For this purpose, the compound is administered topically at a dose of 1-500 µg. 1 to 4 times daily until the desired effect is obtained.

The PGE, especially $PGE_2$, $PGF_\alpha$, and $PGF_\beta$ compounds are useful in the induction of labor in pregnant female animals, including man, cows, sheep, and pigs, at or near term [Karim et al, *J. Obstet. Gynaec. Brit. Cwlth.*, 77:200-210, 1970] or in the induction of therapeutic abortion [Bygdeman et al., *Contraception*, 4, 293 (1971)]. For this purpose, the compound is infused intravenously at a dose of 0.01 to 50 µg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. Alternative routes of administration are oral, extraammiotic or intraammiotic.

The PGE, $PGF_\alpha$, and $PGF_\beta$ compounds are useful for fertility control in female mammals [Karim, *Contraception*, 3, 173 (1971)] including humans and animals such as monkeys, rats, rabbits, dogs, cattle, and the like. By the term ovulating female mammals is meant animals which are mature enough to ovulate but not so old that regular ovulation has ceased. For that purpose, $PGF_{2\alpha}$, for example, is administered systemically at a dose level in the range 0.01 mg. to about 20 mg. per kg. of body weight of the female mammal, advantageously during span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

Patents have been obtained for several prostaglandins of the E and F series ad inducers of labor in mammals (Belgian Pat. No. 754,158 and West German Pat. No. 2,034,641), and on $PGE_1$, $F_2$ and $F_3$ for control of the reproductive cycle (South African Pat. No. 69/6089). It has been shown that luteolysis can take place as a result of administration of $PGF_{2\alpha}$ [Labhsetwar, Nature, 230, 528 (1971)] and hence prostaglandins have utility for fertility control by a process in which smooth muscle stimulation is not necessary.

The PGE and $PGF_2$ compounds are useful as antiarrhythmic agents (Forster, et. al., *Prostaglandins*, 3, 895 (1973)). For this purpose the compound is infused intravenously at a dose range of 0.5-500 µg/kg/minute until the desired effect is obtained.

As mentioned above, the PGE compounds are potent antagonists of epinephrine-induced mobilization of free fatty acids. For this reason, these compounds are useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGE and PGB compounds promote and accelerate the growth of epidermal cells and keratin in animals, including humans, useful domestic animals, pets, zoological specimens, and laboratory animals. For that reason, these compounds are useful in promoting healing of skin which has been damaged, for example, by burns, wounds, and abrasions, surgery, etc. These compounds are also useful in promoting adherence and growth of skin autografts, especially small, deep (Davis) grafts which are intended to cover skinless areas by subsequent outward growth rather than initially, and to retard rejection of homografts.

To promote the growth of epidermal cells, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, such as when there is substantial fluid loss as in the case of extensive burns or skin loss due to other causes, systemic administration is advantageous. Especially in topical applications, these prostaglandins may be advantageously combined with antibiotics such as gentamycin, neomycin, polymyxin B, bacitracin, spectinomycin, tetracycline and oxytetracycline; with other antibacterials such as mafenide hydrochloride, sulfadiazine, furazolium chloride, and nitrofurazone; and with corticosteroids such as hydrocortisone, prednisolone, methylprednisolone, and fluprednisolone, each being used in the combination at the usual concentration suitable for its use alone.

In the preparation of synthetic pharmaceutical agents, among the principal objects is the development of analogs of naturally occurring compounds which are highly selective in their physiological activity and which have an increased duration of activity. In a series of compounds like the naturally-occurring prostaglandins which has an extremely broad activity spectrum, increasing the selectivity of a single compound usually involves the enhancement of one physiological effect and the diminution of the others. By increasing the selectivity, one would, in the case of the natural prostaglandins, expect to alleviate the severe side effects, particularly the gastrointestinal one frequently observed following systemic administration of the natural prostaglandins.

In order to achieve increased selectivity and duration of action in the prostaglandin series, many researchers have concentrated on the molecular modification of the last five carbons of the methyl-terminated side chain. One modification consists of removing one to four carbon atoms from the end of the lower side chain and terminating the chain with an aryloxy or heteroaryloxy group. Compounds of this type are described, for instance, in British Pat. No. 1,350,971, the published Dutch Patent Application No. 73/06462 and Belgian Pat. No. 806,995.

The 11-desoxy analogs of the natural prostaglandins have also been described, for instance, in the published Dutch patent publication No. 16,804, Belgian Pat. No. 766,521 and the West German Offenlegungsschrift No. 2,103,005.

The 11-desoxy analogs described below have been found to be more potent, longer acting, and more selective and possess unanticipated activities when compared to the 11-desoxy analogs of the natural prostaglandins. The present state of the art of knowledge about structure-activity correlations in the prostaglandins does not, however, permit one to explain the observed enhancement of selectivity in the 11-desoxy compounds.

SUMMARY OF THE INVENTION

In accordance with the present invention, there are provided optically active compounds of the structure

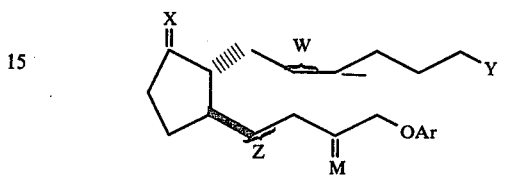

their optical antipodes and racemic mixtures thereof wherein

X and M are selected from the group consisting of keto,

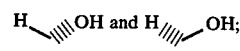

W is a single bond or a cis double bond and Z is a single, trans double or triple bond with the proviso that when Z is a triple bond, W is a cis double bond; Y is selected from the group consisting of 5-tetrazolyl,

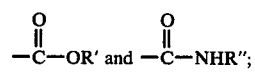

and Ar is selected from the group consisting of phenyl monosubstituted phenyl and α- and β-naphthyl, R' is selected from the group consisting of hydrogen, alkyl of from one to ten carbon atoms, aralkyl of from seven to nine carbon atoms, cycloalkyl of from three to eight carbon atoms, phenyl, monosubstituted phenyl and α- and β-naphthyl, R" is selected from the group consisting of alkanoyl of from two to five carbon atoms, cycloalkanoyl of from four to seven carbon atoms, benzoyl, monosubstituted benzoyl, alkylsulfonyl of from one to four carbon atoms, phenylsulfonyl and monosubstituted phenylsulfonyl, The above-mentioned monosubstituent on the phenyl, benzoyl and phenylsulfonyl radicals is selected from the group consisting of fluoro, chloro, bromo, trifluoromethyl, lower alkyl, lower alkoxy and phenyl.

Among the possible choices for Ar, phenyl and tolyl, especially m-tolyl, are preferred. When Y is —(C=O)—OR', the preferred choices for R' are hydrogen and p-biphenyl, and when Y is —(C=O)NHR", the preferred choices for R" are benzoyl and methylsulfonyl.

Among the tetrazole compounds, the preferred structures are

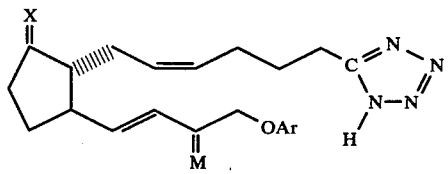

and

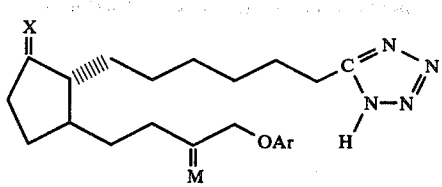

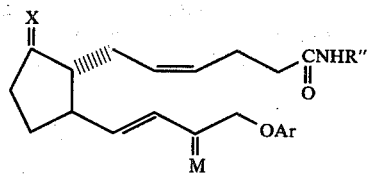

especially when X is keto and when Ar is tolyl, preferably m-tolyl. The preferred compounds are 15α- and 15β-hydroxy and 2-descarboxy-2-(tetrazol-5-yl)-9,15-dioxo-16-m-tolyloxy-cis-5-trans-13-ω-tetranorprostadienoic acid and the corresponding 13,14-dihydro-PGE₁ compounds.

Among the acids and esters, the preferred structures are

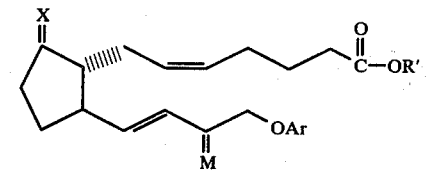

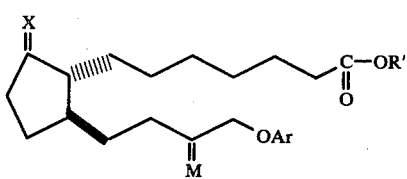

and their optical antipodes especially when R' is hydrogen or p-biphenyl, when Ar is phenyl or tolyl and preferably m-tolyl, and when X is keto. Among the preferred compounds are 15α- and 15β-hydroxy and 15-oxo-9-oxo-16-m-toloxy-cis-5-trans-13-ω-tetranorprostadienoic acids, and their optical antipodes, their p-biphenyl esters and their antipodes and the corresponding 13,14-dihydro-PGE₁ compounds and their antipodes. Also of interest are the above compounds in which the m-tolyl group is replaced by a phenyl group. Of particular interest is ent-9-oxo-15α-hydroxy-16-phenoxy-cis-5-trans-13-ω-tetranorprostadienoic acid. Also of interest in the acid series are compounds of the structure

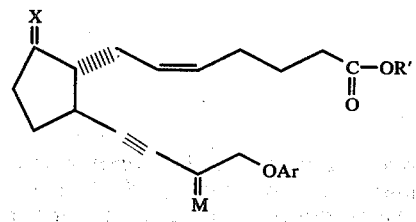

especially when Ar is phenyl or β-naphthyl and when X is keto or α-hydroxy. It is generally preferred that R' be hydrogen. Among the preferred compounds are 9-oxo and 9α-hydroxy-15-hydroxy-16-phenoxy-ω-tetranorprosta-cis-5-ene-13-yneoic acids.

Among the preferred amide structures is especially when M or X are keto, R" is benzoyl or methylsulfonyl and Ar is tolyl, especially m-tolyl, or phenyl.

The tetrazole compounds of the present invention are principally useful as fertility control agents and abortifacients or labor inducers. To induce labor, the compounds are infused intravenously at a rate of about 0.01 to 50 μg/kg body weight/min until about the termination of the second stage of labor. To control ovulation, the compounds are administered systemically at a dose level of about 0.01 to 20 mg/kg of body weight. The acids and amides are useful principally as antiulcer agents. For the treatment of peptic ulcers, these compounds are administered orally in the form of tablets or capsules at doses of 0.2 to 20 mg/kg/day. The 9-oxo-15(α or β)-hydroxy-16-phenoxy-cis-5-trans-13-tetranorprostadienoic acids, their p-biphenyl esters and the optical antipodes of both are particularly useful as both antiulcer and antisecretory agents. The compounds are usually administered orally at a dose of 0.1 to 100 μg/kg of body weight.

Unexpectedly, the 11-deshydroxy compounds of the present invention exhibit good smooth muscle stimulating activity as exhibited by their ability to induce labor or abortion and to regulate the menstrual cycle. In contrast, 11-deshydroxy PGE₂ exhibits virtually no smooth muscle stimulating activity whatsoever.

DETAILED DESCRIPTION OF THE INVENTION

As shown in Scheme A, the first step (1→2) is a condensation between the known aldehyde 1 (Corey and Ravindranathan, *Tetrahedron Lett.*, 1971, 4753) with an appropriate 3-keto phosphonate to produce enone 2. The keto phosphonate is usually produced by condensation of the appropriate carboxylic acid ester with a dialkyl methyl phosphonate. Typically the desired methyl ester is condensed with dimethyl methyl phosphonate.

Enone 2 then reduced to enol 3 with zinc borohydride or a hindered alkyl borohydride such as lithium triethylborohydride or potassium tri-sec-butylborohydride. This reduction produces a mixture of epimers both of which may be used as substrates for further reactions. 3 is used to produce prostaglandin analogs having an α-hydroxyl at C₁₅. The epimer of 3 is used to produce prostaglandin analogs having a β-hydroxyl at C₁₅. In addition, the mixture of C₁₅ epimers may be used to produce 15-keto prostaglandin analogs. The epimers produced in the hydride reduction can be separated by column, preparative thin layer, or preparative high pressure liquid chromatography. In the reduction reaction, ethers such as tetrahydrofuran or 1,2-dimethoxyethane or acetonitrile are usually employed as solvents.

Enone 2 may be reduced catalytically with hydrogen to ketone 6, a suitable starting material for the preparation of 13,14-dihydro prostaglandin analogs of the present invention. This reduction may be achieved with either a homogeneous catalyst such as tris-tri-phenylphosphinerhodiumchloride or with a heterogeneous catalyst system such as platinum, palladium or rhodium. The stage at which the reduction is carried out is not critical as will be seen below.

medium or dimethyl-tert-butylsilyl chloride and imidazole, respectively.

(4→5) is a reduction of the lactone 4 to hemiacetal 5 using a suitable reducing agent such as disobutyl alumi-

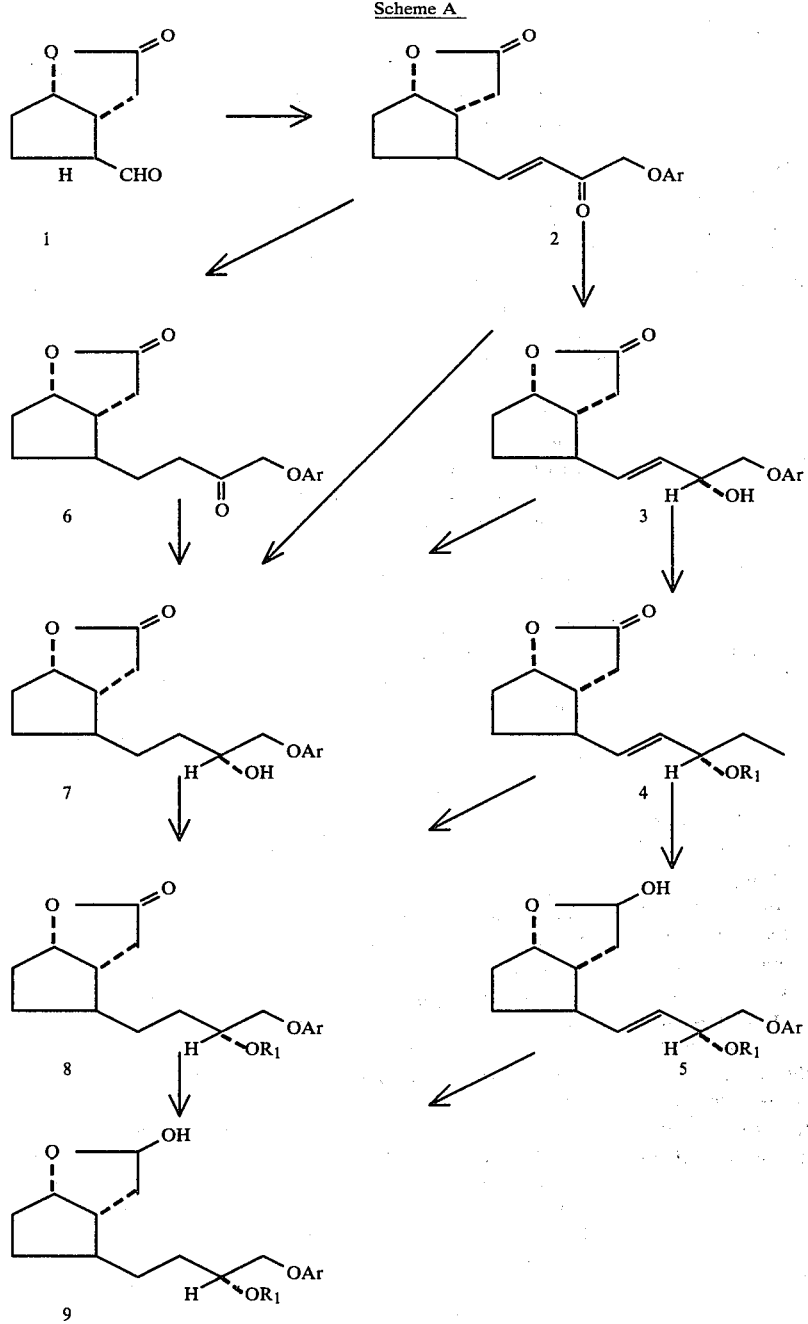

Scheme A

Enone 2 may also be reduced with borohydride ion to produce a mixture of the alcohol 7 and its $C_{15}$ epimer in a single step or alternatively, enol 3 may be catalytically reduced to produce the same epimer mixture.

(3→4) involves the protection of the free hydroxyl group with an acid labile protecting group ($R_1$). Any sufficiently acid labile group is satisfactory, however, the most usual ones are tetrahydropyranyl or dimethyl-tert-butylsilyl which can be incorporated in the molecule by treatment with dihydropyran and an acid catalyst, usually p-toluenesulfonic acid, in an anhydrous num hydride in an inert solvent. Low reaction temperatures are preferred and $-60$ to $-80°$ C. are usual. However, higher temperatures may be employed if overreduction does not occur. 5 is then purified if desired by column chromatography. As indicated in Scheme A, compounds 4 and 5 may be catalytically reduced to 8 and 9 respectively, by the procedure outlined above.

The conversion of (6→9) follows that already outlined by the conversion of (2→5).

The remainder of the synthesis of the two- series prostaglandin analogs of this invention is outlined in Scheme B. (5→10) is a Wittig condensation in which hemiacetal 5 is reacted with 4-(substituted) butyltriphenylphosphonium (22) bromide in dimethyl sulfoxide in the presence of sodium methylsulfinyl methide. The substituent in the 4-position (Y) may be —COOH or tetrazol-5-yl. 10 is then purified as above. The conversion of 10→11 is an acid catalyzed hydrolysis of protecting group. Any acid may be used which does not cause destruction of the molecule in the course of the removal of the protecting group, however this is accomplished most often by the use of 65% aqueous acetic acid. Alternatively, the dimethyl-tert-butylsilyl protecting group may be removed by the action of tetraalkylammonium fluoride in a solvent such as tetrahydrofuran. The product is purified as above.

11 is an 11-desoxy-16-aryloxy-ω-tetranorprostaglandin of the $F_{2\alpha}$ series. The prostaglandin analogs of the $E_2$ series of this invention (13) are prepared from intermediate 10 which may be oxidized by any reagent capable of oxidizing hydroxyl groups which does not attack double bonds. However, the Jones reagent is usually preferred. The product is purified as above to produce intermediate 12. Intermediate 12 may be converted into the prostaglandin analogs of the $E_2$ series (13) of this invention in the same manner as described for (10→11). Furthermore, intermediate 12 may be reduced with sodium borohydride to a mixture of intermediate 15 and its $C_9$ epimer which are separable by column, preparative thin layer, or preparative high pressure liquid chromatography and which can be converted into prostaglandin analogs of the $F_{2\alpha}$ and $F_{2\beta}$ series of this invention by the methods given for (10→11). Alternatively, compound 13 may be reduced with sodium borohydride to provide the $F_{2\alpha}$ and $F_{2\beta}$ prostaglandin analogs of this invention directly. This epimeric mixture may be separated as described above for 15 to provide pure $PGF_{2\alpha}$ and $PGF_{2\beta}$.

Scheme B

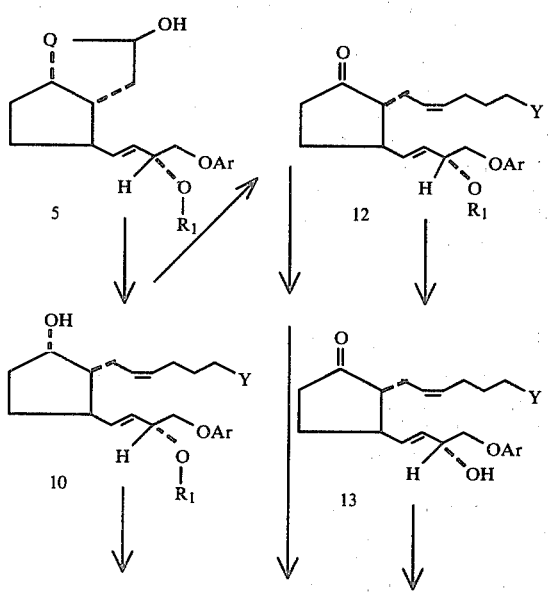

-continued
Scheme B

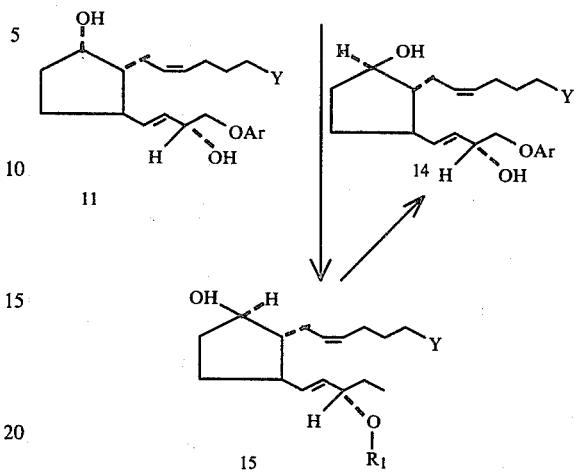

The variious reduced prostaglandin analogs of this invention, that is, prostaglandins of the one, zero and 13,14-dihydro-two series are produced as shown on Scheme C. Intermediate 6 may be converted to 19 by the steps already outlined for the conversion of (2→10). 19 may then be converted to 20 by the steps discussed above for the conversion of (10→15). 20 may be catalytically reduced to produce 18 ($R_1$=THP or $(CH_3)_2Si\ C(CH_3)_3$) which is the precursor for the prostaglandin analogs of the zero series of this invention by the steps previously outlined. Palladium or platinum on carbon are, among others, useful catalysts in this reduction.

(16→17) is a selective catalytic hydrogenation of the 5-6 cis double bond at low temperature using catalysts such as those described above. Especially preferred for this reduction is the use of palladium on carbon as a catalyst and a reaction temperature of about −20° C. 17 ($R_1$=THP or $(CH_3)_2\ Si\ C(CH_3)_3$) is not only a precursor for the prostaglandin analogs of the "one" series of this invention but also for the "zero" series since 17 may be reduced to 18 reducing the methods described for (4→8). Similarly, 16 may be reduced to 18 by the same procedure. The removal of the protecting groups is carried out as previously described and 17, 18, 19 and 20 wherein $R_1$=THP or $(CH_3)_2\ Si\ C(CH_3)_3$) may be deprotected in this way to produce prostaglandins of the "one", "zero", and 13,14-dihydro series of this invention. The production of prostaglandins of the E and F series wherein said prostaglandin is of "zero", "one", or 13,14-dihydro-two series from 16, 17, 18, 19 and 20 follows that previously described for the conversion of 10 11, 12, 13, 14, and 15.

Scheme C

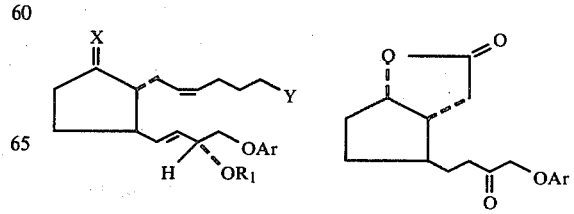

Scheme C
-continued

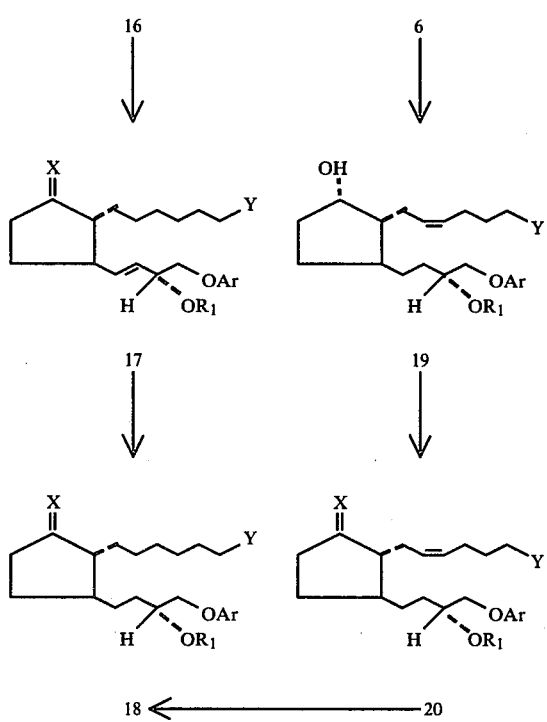

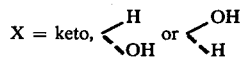

$R_1$ = H, THP or $(CH_3)_2 Si C(CH_3)_3$ $X$ = keto, $\overset{H}{\underset{OH}{<}}$ or $\overset{OH}{\underset{H}{<}}$ Furthermore, the 11-desoxy-16-substituted-ω-tetranorprostaglandin analogs of the $E_1$, $F_{1\beta}$ and $F_{1\alpha}$ series may be obtained directly from the corresponding prostaglandin analog of the "2-series", by first protecting the hydroxyl by introducing dimethylisopropyl silyl groups reducing selectively the cis double bond, and removing the protecting group.

The reduction is usually accomplished as discussed above for (16→17) and removal of the protecting group is accomplished by contacting the reduced protected compound with 3:1 acetic acid: water for 10 minutes or until reaction is substantially complete.

The 11-desoxy-16-substituted-ω-tetranorprostaglandin analogs of the "one" series of this invention may be prepared by the alternate synthesis summarized in Scheme D. For the first step in the preparation of the above named prostaglandin analogs, the hemiacetal 2-[5α-hydroxy-2β-benzyloxymethylcyclopent-1α-yl]-acetaldehyde, γ-hemiacetal is caused to react with the disodium salt of 4-(substituted)butyltriphenylphosphonium bromide (22) as described above for 5 10. The substituent in the 4-position is again the above-mentioned Y. This intermediate may be converted by procedures described in detail in the appended examples as summarized below.

As shown in Scheme D, hemiacetal 21 is caused to react with the reagent 22 to produce 23.

Scheme D

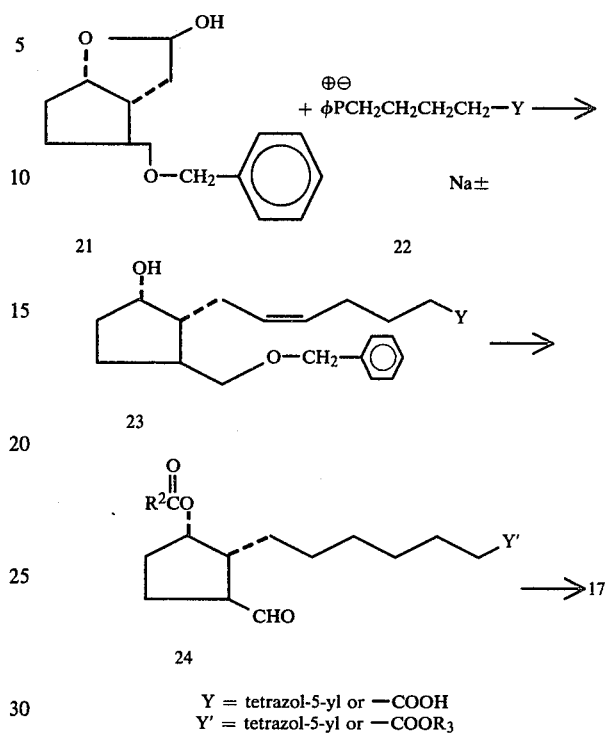

$Y$ = tetrazol-5-yl or —COOH
$Y'$ = tetrazol-5-yl or —COOR$_3$

If Y is COOH rather than tetrazol-5-yl, 23→24 involves esterifying the carboxyl group with diazomethane to form a methyl ester intermediate. Other blocking groups may be used provided the group is stable to hydrogenation and mild acid hydrolysis and removable by mild basic hydrolysis. Such groups ($R_3$) include alkyl of from 1 to 10 carbons, phenalkyl of up to 9 carbons, phenyl, mono-substituted phenyl including tolyl and p-biphenyl, or α- or β-naphthyl.

Acylation of the 9-hydroxy group of the methyl ester intermediate with acetic anhydride and pyridine forms an acetate intermediate. Other blocking groups may be used provided the group is stable to hydrogenation and mild acid hydrolysis. Such groups ($R_2$) include alkyl or from 1 to 9 carbons, phenalkyl of up to 9 carbons, phenyl, tolyl, p-biphenyl or α- or β-naphthyl. The protected benzyl ether upon reduction with hydrogen and palladium on carbon in an appropriate solvent containing a suitable acid catalyst, ethanol and acetic acid or ethyl acetate and hydrochloric acid being especially preferred, affords a hydroxy compound oxidation of which with Collins' reagent of Pfitzner-Moffatt oxidation yields aldehyde 24.

24→17 involves treatment of 24 with the sodium salt of the appropriate 3-ketophosphonate under conditions described for 1→2, to form an enone reduction of which with a hindered alkyl borohydride such as lithium triethylborohydride or potassium tri-sec-butylborohydride or zinc borohydride forms an enol. The hydroxyl group is then protected by treatment with dihydropyran to form a 2-tetrahydropyranyl ether. Other protecting groups may be employed provided they are stable to mild basic hydrolysis and easily removable by mild acid hydrolysis. Such groups include dimethyl-t-butylsilyl. This protected compound is then contacted with aqueous sodium hydroxide to yield 17. The conversion of 17 to the 11-desoxy-16-aryloxy-ω-tetranorprostaglandins of the "one" series of this invention follows the procedure outlined above.

11-desoxy-15-keto-16-aryloxy-ω-tetranorprostaglandins E of this invention may be prepared as summarized in Scheme E. 25→26 involves oxidation of the C$_9$ and/or C$_{15}$ alcohol moieties of 25. Any reagent capable of oxidizing hydroxyl groups which does not attack double bonds may be used, however, the Jones' reagent is usually preferred. The 15-keto-prostaglandin E analogs of this invention of the 13,14-dihydro two-, one-, and zero- series may be prepared from compounds 27, 29 and 31 as described for 25→26 above.

Scheme F summarizes the preparation of the 11-desoxy-15-keto-16-aryloxy-ω-tetranorprostaglandin F$_{2\alpha}$ and F$_{2\beta}$ analogs of this invention. 33→34 involves acylation of 33 at the 9-position with acetic anhydride and pyridine to form an acetate intermediate. Other blocking groups may be used provided the group is stable to mild acid hydrolysis. Such groups include alkanoyl of from 2 to 9 carbons, phenalkanoyl of up to 10 carbons, benzoyl, tolyl, p-phenylbenzoyl, or α- or β-naphthoyl. The protecting group at C$_{15}$ is then removed as described above to provide a second intermediate. The next step involves oxidation of the C$_{15}$ alcohol moiety to provide a third intermediate. Any reagent capable of oxidizing hydroxyl groups which does not attack double bonds may be used, however, the Jones' reagent is usually preferred. The last step in this sequence involves transesterification of the protecting group at C$_9$.

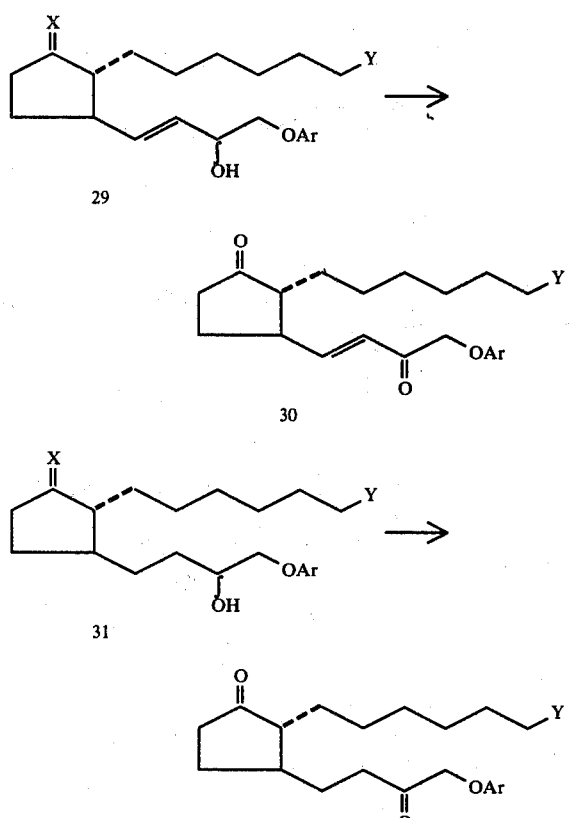

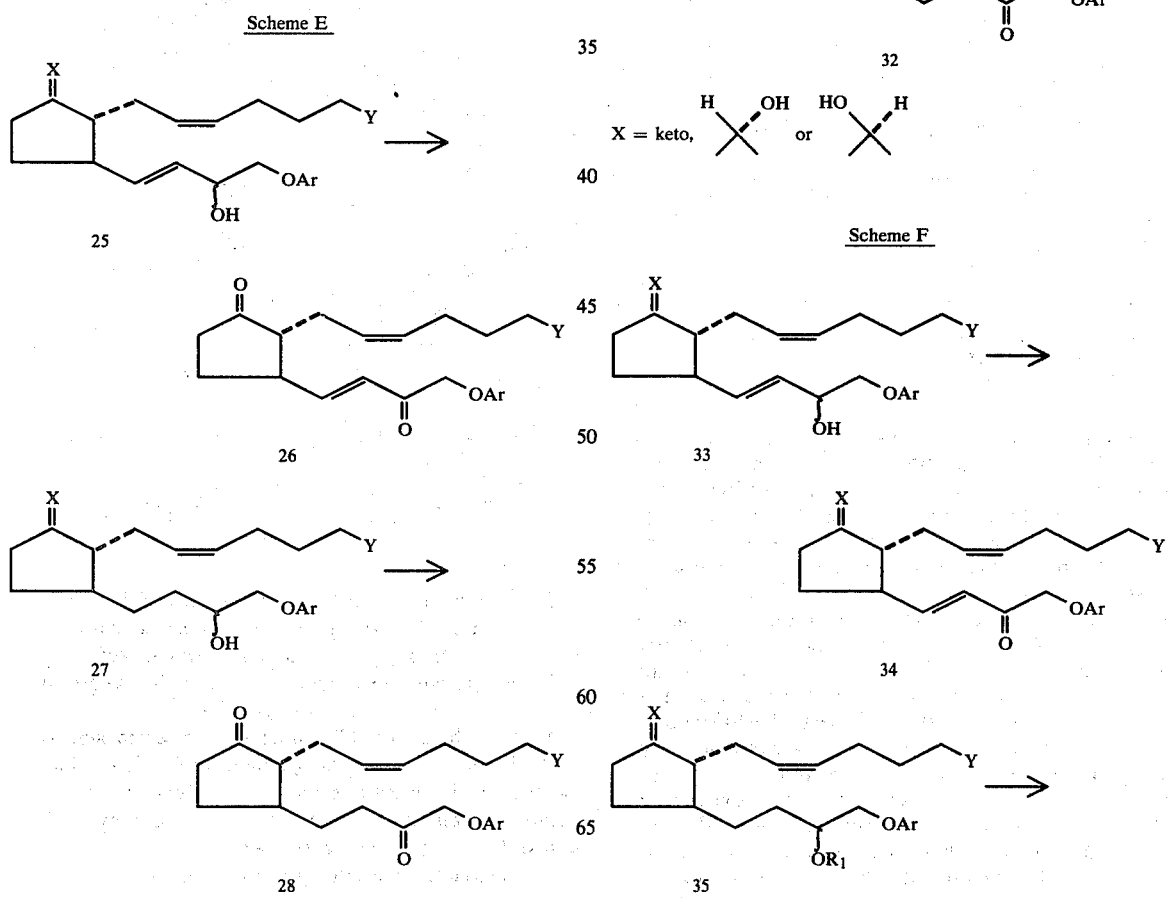

-continued
Scheme F

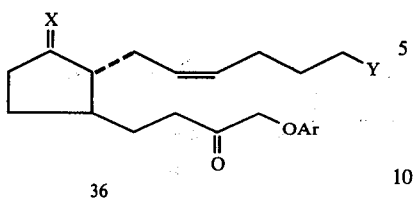

36

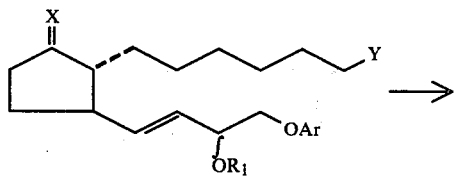

37

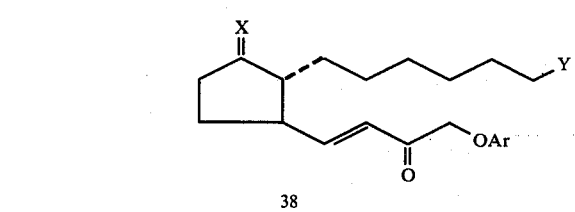

38

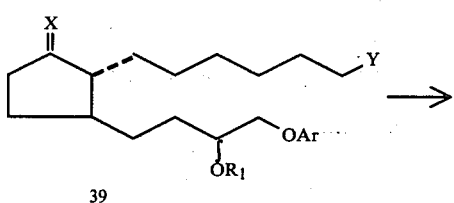

39

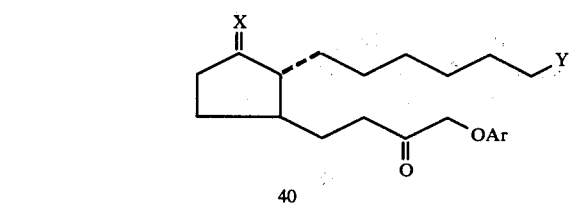

40

$R_1$ = THP or $(CH_3)_2 SiO(CH_3)_3$

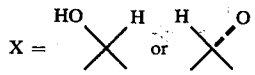

This is usually done by treatment with anhydrous potassium carbonate in an alcoholic solvent such as methanol, which affords the 15-keto $F_{2\alpha}$ or $F_{2\beta}$ analogs of this invention. The 15-keto-prostaglandin $F_\alpha$ of $F_\beta$ analogs of the present invention of the 13,14-dihydro-two-, one-, and zero- series may be prepared from compounds 35, 37, and 39 and described for 33→34. It should be noted that the stereochemistry of the hydroxyl group at $C_{15}$ is unimportant for the preparation of all 15-keto compounds of the present invention; 15β, 15α, or an epimeric mixture will all afford the same 15-keto analog. The preparation of the 13,14-dehydro $PGE_2$ and $PGF_2$ analogs is shown in Scheme G. 41 is prepared by adding 1 to a solution of triphenylphosphine and carbon tetrabromide in a suitable solvent such as methylene bromide under an inert atmosphere at about 0° C.

The γ-lactone 41 is then reduced to a γ-hemiacetal with diisobutylaluminum hydride as in (8→9) above and converted to the γ-methylacetal by treatment with anhydrous methanol in the presence of boron trifluoride. This compound is then dissolved in tetrahydrofuran, cooled to dry ice temperatures under an inert atmosphere and treated with butyl lithium to produce 42. Actually, a mixture of epimeric γ-methylacetals is produced and only the α-epimer is shown in 42.

42 is then dissolved in tetrahydrofuran, treated with butyl lithium at about 0° C. under an inert atmosphere and then cooled to dry ice temperatures. This mixture is then treated with an aryloxyacetaldehyde to produce 43 which is purified by column chromatography. Actually, a mixture of hydroxy epimers is produced with only the α-epimer shown in 43.

Scheme G

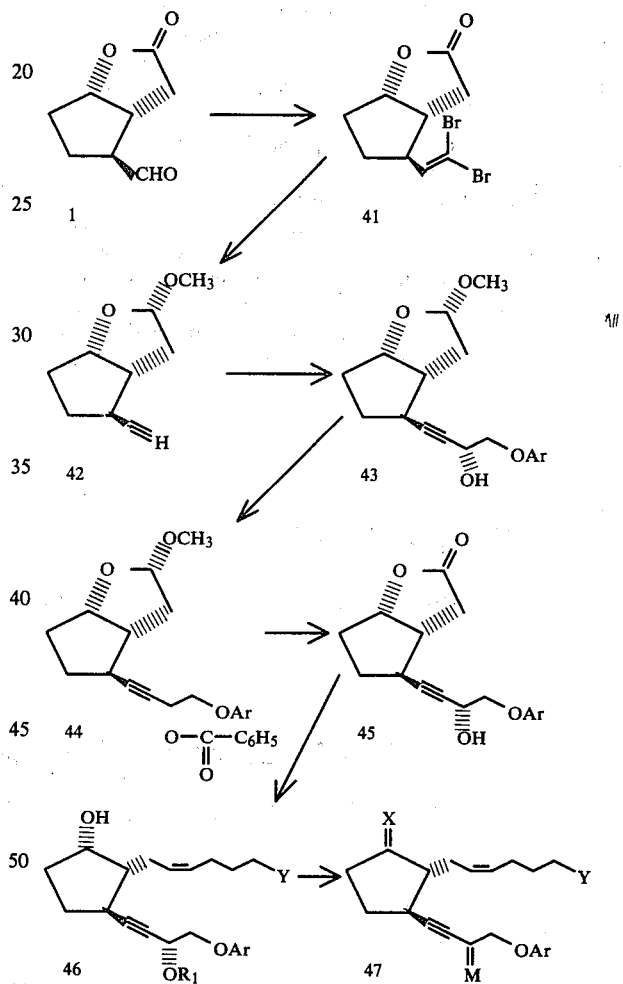

The free hydroxyl group is then esterified with a suitable acid chloride, preferably benzoyl chloride which is not easily subject to hydrolysis in acid and which will prevent the oxidation of the hydroxyl group by Jones reagent. This process yields 44.

The γ-methylacetal 44 is then solvolyzed in acid is tetrahydrofuran to yield the γ-hemiacetal which is then oxidized to the γ-lactone with Jones Reagent. The γ-lactone is then treated with potassium carbonate in methanol to yield the γ-lactone 45.

The acid labile protecting group ($R_1$) is introduced as in (45→46) as in (3→4) above. The γ-lactone is then reduced to the γ-hemiacetal to produce 46 as in 4→5 above.

The first step in (45→47) involves the reaction of 45 with an appropriate 4-(substituted)butyltriphenylphosphonium bromide (22) in dimethyl sulfoxide in the presence of sodium methylsulfinyl methide. This reaction yields the 9α-hydroxy compound 46. The removal of the acid labile protecting group ($R_1$) in 46 as in (10→11) above yields 47 as a mixture of 15-hydroxy epimers which are separable by column, preparative thin layer of preparative high pressure liquid chromatography.

The 9-keto-11-desoxy-15-keto-16-aryloxy-13,14-dehydro-ω-tetranorprostaglandins may be produced by oxidation of the epimeric mixture of 9α-hydroxy-15-hydroxy compounds of structure 47 mentioned above. Any agent capable of oxidizing hydroxy groups which does not attack double bonds may be used. However the Jones reagent is usually preferred.

The 9β-hydroxy-15-hydroxy compounds may be produced from the 9α-hydroxy-15-protected hydroxy compound 46 as described in (10→12→15→14) above. If one begins with a mixture of $C_{15}$ epimers one will obtain a mixture which may be separated as above.

The 9-keto-15-hydroxy compounds are prepared by first oxidizing a 9-hydroxy-15-protected hydroxy compound 46 with Jones reagent or any other suitable reagent which will oxidize hydroxy groups but not double bonds and then solvolyzing the protecting group in acid as described above. Again, if one begins with a mixture of $C_{15}$ epimers, one obtains a mixture which may be separated as above.

As indicated above, the acids and tetrazoles may be prepared directly by reacting [4-(tetrazol-5-yl)butyl] or [4-(carboxy)butyl]triphenylphosphonium bromide with the appropriate γ-hemiacetal as, for instance, in (5→10) above. The N-substituted amides may also be prepared in this manner. For instance, if [4-(methanesulfonylaminocarbonyl)butyl]triphenylphosphonium bromide may be reacted directly with 2-[5α-hydroxy-2β-(3α-[tetrahydropyran-2-yloxy]-4-phenoxy-trans-1-buten-1-yl) cyclopent-1α-yl]acetaldehyde, γ-hemiacetal to produce the corresponding 11-desoxy-15-THP-PGF$_{2α}$ which may then be subjected to acid hydrolysis to form the 15-hydroxy compound and then oxidized with Jones reagent to form the corresponding 11-desoxy-15-keto-PGE$_2$.

An alternative route to the amides involves contacting a prostanoic acid with only keto or protected hydroxy groups at the 9- and 15-positions with an isocyanate of the structure R″—N═C═O. The compounds are contacted in reaction-inert solvent such as dry tetrahydrofuran in the presence of a base such as triethylamine. Reaction-inert solvents are those which are substantially free of adverse effects on reactants and products under th conditions employed. As an example of the above reaction, benzoyl isocyanate may be contacted with 9-keto-15-keto-cis-5-trans-13-16-(m-tolyloxy)-ω-tetranorprostadienoic acid to form the corresponding 15-keto-PGE$_2$-N-benzoyl amide.

The assignment of the configuration at $C_{15}$ is made on the gasis of mobilites in thin layer chromatography of the alcohols and $C_{15}$ epi-3. It is assumed that the less polar higher $R_f$) epimer has the 15α-hydroxy configuration and the more polar (low $R_f$) epimer has the 15β-hydroxy configuration. Among the suitable solvent systems are mixtures of ether or ethyl acetate in benzene. This assignment of $C_{15}$ configuration is based on this observed for the synthesis of the natural prostaglandins (Corey, et al., *J. Am. Chem. Soc.*, 93, 1491 (1971)).

Phenyl and substituted phenyl esters of the present invention are prepared by contacting a prostanoic acid with an appropriate phenol in reaction-inert solvent such as dry methylene chloride in the presence of a coupling agent such as dicyclohexylcarbodiimide or diethylcarbodiimide. For instance, ent keto-11-desoxy-15β-hydroxy-16-phenoxy-cis-5-trans-13-ω-tetranorprostadien acid may be contacted with p-phenylphenol in dry methylene chloride in the presence of dicyclohexylcarbodiimide to form the corresponding ester. Alkyl and phenalkyl esters of the present invention may be prepared by contacting a prostanoic acid with an appropriate diazoalkane in a reaction-inert solvent such as ether or tetrahydrofuran. Alternatively, the esters of the present invention may be prepared by first contacting a prostanoic acid with pivaloylchloride in a reaction inert solvent such as ether in the presence of an appropriate base such as triethylamine and then treating the resultant intermediate with an appropriate alcohol. Beginning with the corresponding PGE$_0$, the same reaction may be carried out.

In the foregoing procedures, where purification by column chromatography is desired, appropriate chromatography supports include neutral alumina and silica gel. The chromatography suitably conducted in reaction inert solvent such as ether ethyl acetate, benzene, chloroform, methylene chloride, cyclohexane and n-heptane, as further illustrated in the appended examples. When purification of high pressure liquid chromatography is desired, appropriate supports include 'Corasil' 'Porasil', and 'Gichrosorb' with inert solvents such as ether, chloroform, methylenechloride, cyclohexane and n-hexane being employed.

It will be seen that the foregoing formulae depict optically active compounds. It is intended that both optical antipodes e.g. 8,12-nat and 8,12-ent, be embraced by the foregoing formulae and in the appended claims. The two optical antipodes are readily prepared by the same methods by mere substitution of the appropriate optically active precursor aldehyde. It will be clear, however, that the corresponding racemates will exhibit valuable biological activity by virtue of their content of the above-mentioned biologically active optical isomers, and it is intended that such racemates also be embraced by the foregoing formulae herein and in the appended claims. The racemic mixtures and readily prepared by the same methods employed herein to synthesize the optically active species, by mere substitution of corresponding racemic precursors in place of optically active starting materials.

In numerous in vivo and in vitro tests we have demonstrated that the new prostaglandin analogs possess physiological activities comparable but much more tissue selective and later acting than these exhibited by the natural prostaglandins (as above). These tests include, among others, a test for effect on dog blood pressure, inhibition of stress-induced ulceration the rat, effect on mouse diarrhea, inhibition of stimulated gastric acid secretion in rats and dogs, spasmogenic effect on isolated guinea pig and rat uterus, protective effect on histamine induced bronchospasm in the guinea pig, and antifertility activity in rats and guinea pigs.

The physiological responds observed in these tests are useful in determining the utility of the test substance for the treatment of various natural and pathological conditions. Such determined utilities include: vasodilator activity, antihypertensive activity, bronchodilator activity, antiarrythmic activity, cardiac stimulant activity, antifertility activity and antiulcer activity.

An advantage possessed by 11-desoxy prostaglandins of the E series in general is their increased stability as compared with such as $PGE_2$. In addition the novel 11-desoxy-16-aryloxy-$\omega$-tetranorprostaglandins of this invention possess highly selective activity profiles compared with the corresponding naturally occurring prostaglandins and, in many cases, exhibit a longer duration of action. The novel prostaglandin tetrazole analogs of this invention possess useful antifertility activity. Prime examples of the therapeutic importance of these prostaglandin analogs is the efficacy of 1-(tetrazol-5-yl)11-desoxy-16-(m-tolyloxy)-$\omega$-tetranoprostaglandin $E_0$ and 1-(tetrazol-5-yl)11-desoxy-16-(m-tolyloxy)-$\omega$-tetranoprostaglandin $E_2$ which exhibit enhanced antifertility activity. At the same time, other physiological activities are markedly depressed in comparison with $PGE_2$.

In addition, 11-desoxy-16-aryloxy-$\omega$)-tetranoprostaglandins of the $E_0$, $E_1$ and $E_2$ series and their esters and amides exhibit a high degree of antiulcer activity. The corresponding 13,14-dihydro $PGE_2$ compounds are potent antisecretory agents.

Another outstanding example of the therapeutic importance of those prostaglandin analogs is the potent and selective antiulcer and antisecretory activity displayed by the 15-keto- and 15-hydroxy-11-desoxy-16-phenoxy-$\omega$-tetranor $PGE_2$ and their optical antipodes. The esters of these compounds, especially the p-biphenyl esters, also possess these desirable gastrointestinal activities.

Pharmacologically acceptable salts useful for the purposes described above are those with pharmacologically acceptable metal cations, ammonium, amine cations, or quaternary ammonium cations. Salts can be formed with the acids, sulfonamides or tetrazoles of the present invention.

Especially preferred metal cations are those derived from the alkali metals, e.g., lithium, sodium and potassium, and from the alkaline earth metals, e.g., magnesium and calcium although cationic forms of other metals, e.g., aluminum zinc and iron, are within the scope of this invention.

Pharmacologically acceptable amine cations are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotamine, cyclopentylamine, dicyclohexylamine, benzylamine, dibenzylamine, $\alpha$-phenylethylamine, 62 -phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, bis(hydroxymethyl)aminomethane, N-phenylethanolamine, N-(p-tetiorylphenyl)-diethanolamine, galactamine, N-methylglucamine, N-methylglucosamine, epherdrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The new compounds of this invention can be used in a variety of pharmaceutical preparations which contain the compound or a pharmaceutically acceptable salt thereof, and they may be administered in the same manner as natural prostaglandins by a variety of routes, such as intravenous, oral and topical, including aerosol, intravaginal, and intranasal, among others.

The 16-aryloxy-$\omega$-tetranoprostaglandin tetrazole analogs of the present invention are useful as antifertility agents. They may be administered systemically or preferably orally intramuscularly or intravaginally at a dose level of 0.01 to about 20 mg/kg of body weight per day.

The 16-aryloxy-$\omega$-tetranorprostaglandin E analogs of the present invention and their esters and amides are useful antiulcer agents. For treatment of peptic ulcers these drugs may be administered orally in the form of capsules or tablets at doses of 0.1 to 20 mg/kg per day. As antisecretory agents the compounds are administered parenterally by injection or intravenous infusion at a daily dosage level of about 0.5 to about 5 mg/kg per day or orally at a daily dosage level of about 0.1 to 20 mg/kg per day.

The 16-aryloxy-$\omega$-tetranoprostaglandin tetrazole analogs of the present invention are useful as agents to synchronize oestrus in domestic animals such as cattle, swine, sheep, and horses. They may be administered intramuscularly at a dose of 0.1 to 10 mg. per infection.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. In these examples it will be appreciated that all temperatures are expressed in Centigrade, all melting and boiling points are uncorrected.

EXAMPLE I

Dimethyl 2-Oxo-3-(m-tolyloxy)propylphosphonate

A solution 69.4 g. (0.555 moles) dimethyl methylphosphonate (Aldrich) in 800 ml. dry tetrahydrofuran was cooled to $-78°$ in a dry nitrogen atmosphere. To the stirred phosphonate solution was added 230 ml. of 2.4 m n-butyllithium in hexane solution (Alfa Inorganics) dropwise over a period of 75 min. at such a rate that the reaction temperature did not rise above $-65°$. After an additional 5 min. at $-78°$, 50 g. (0.277 mole) methyl 2-m-tolyloxy acetate was added rapidly (5 min.). After 3.5 hrs. at $-78°$, the reaction mixture was allowed to warm to ambient temperature, neutralized with 50 ml. acetic acid and rotary evaporated to a white gel. The galatinous material was taken up in 175 ml. water, the aqueous phase extracted with 100 ml. portions of chloroform ($3\times$), the combined organic extracts were backwashed (50 cc $H_2O$), dried and concentrated to a crude residue and distilled, b.p. 159°–164° (0.15 mm) to give 40 g. dimethyl 2-oxo-3-m-tolyloxypropylphosphonate.

The nmr spectrum (CDCl₃) showed a doublet centered at 3.75 δ(J=11.5 cps, 6 H) for

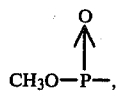

a singlet at 4.70 δ (2 H) for C₇H₈—O—CH₂—CO—, a doublet centered at 3.24 δ (J=23 cps, 2 H) for

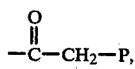

a singlet at 2.30 δ (3 H) for the methyl and a multiplet at 6.8–7.5 δ (4 H) for the aromatic protons.

In similar fashion, a series of 2-oxo-3-(aryloxy)-propylphosphonates may be prepared in which any of the above-mentioned Ar is the aryl substituent. For example, Ar may be

| Ar | Ar |
|---|---|
| (p-phenyl)phenyl | (p-bromo)phenyl |
| phenyl | (o-chloro)phenyl |
| p-tolyl | (p-ethoxy)phenyl |
| (p-trifluoromethyl)phenyl | (p-fluoro)phenyl |
| α-naphthyl | (p-ethyl)phenyl |
| β-naphthyl | (o-methoxy)phenyl |
| (p-methoxy)phenyl | (m-methoxy)phenyl |
| (o-fluoro)phenyl | (m-fluoro)phenyl |
| (p-chloro)phenyl | (p-isopropyl)phenyl |
| (m-phenyl)phenyl | (p-butyl)phenyl |
| (m-ethyl)phenyl | (m-trifluoromethyl)phenyl |
| (m-bromo)phenyl | (m-chloro)phenyl |
| o-tolyl | (o-bromo)phenyl |
| (o-trifluoromethyl)phenyl | (p-isopropoxy)phenyl |

EXAMPLE II

2-[5α-Hydroxy-2β-(3-oxo-4-m-tolyloxy-trans-1-buten-1-yl)cyclopent-1α-yl]acetic acid, γ-lactone (2)

Dimethyl 2-oxo-3-m-tolyloxy propylphosphonate 8.05 g., (31 mmole), in 100 ml. dry tetrahydrofuran was treated with 1.1 g. (28.6 mmole) sodium hydride (Alfa Inorganics) in a dry nitrogen atmosphere at room temperature. After 50 min. of stirring, a solution of 4 g. (26 mmole) 2-[5α-hydroxy-2β-formyl-cyclopent-1α-yl]acetic acid, γ-lactone (1) in 25 ml. of dry tetrahydrofuran was added dropwise over 10 min. After 30 min. the reaction was quenched with 6 ml. glacial acetic acid, diluted with ether and washed with 100 ml. saturated sodium bicarbonate (2×), 100 ml. water (2×) and 100 ml. saturated brine (1×), dried (Na₂SO₄) and evaporated to yield 4.6 g. 2[5α-hydroxy-2β-(3-oxo-4-m-tolyloxy-trans-1-buten-1-yl)cyclopent-1α-yl]acetic acid, γ-lactone(2) as an oil after column chromatography (silica gel, Baker, 60–200 mesh).

The ir spectrum (CHCl₃) of the product exhibited absorption bands at 1775 cm⁻¹ (strong), 1715 cm⁻¹ (strong), 1675 cm⁻¹ (medium) and 1630 cm⁻¹ (medium) attributable to the carbonyl groups and at 970 cm⁻¹ for the trans double bond.

In similar fashion, the dimethyl-2-oxo-3-(aryloxy)-propylphosphonates of Example I may be reacted with (1) to form the corresponding 2β-substituted Wittig condensation products.

EXAMPLE III

2-[5α-Hydroxy-2β-(α-hydroxy-4-m-tolyloxy-trans-1-buten-1-yl)-cyclopent-1α-yl]acetic acid, γ-lactone (3)

To a solution of 4.6 g. (15.3 mmole) 2-[5α-hydroxy-2β-(3-oxo-4-m-tolyloxy-trans-1-buten-1yl)cyclopent-1α-yl]acetic acid, γ-lactone (2) in 50 ml. dry tetrahydrofuran was cooled to −78° in a dry nitrogen atmosphere. Lithium triethylborohydride (Aldrich), 16.8 ml. (16 mmole) was added dropwise over 15 min. After stirring at room temperature for 30 min., the reaction was quenched with 10 ml. of aqueous acetic acid and allowed to warm to room temperature. The reaction mixture was concentrated by rotary evaporation, taken up in ether and washed with 100 ml. water (2×) and 100 ml. brine (2×). After drying (Na₂SO₄) and concentrating the resultant oil was purified by column chromatography on silica gel (Baker "Analyzed" Reagent) using either as eluent. After elution of less polar impurities, a fraction containing 1.5 g. 2[5α-hydroxy-2β-(3α-hydroxy-4-m-tolyloxy-trans-1-buten-1-yl) cyclopent-1α-yl]acetic acid, γ-lactone (3), a 400 mg. fraction of mixed 3 and epi-3 and finally a fraction containing 1.7 g. 2[5α-hydroxy-2β-(3β-hydroxy-4-m-tolyloxy-trans-1-buten-1-yl)cyclopent-1α-yl]acetic acid, γ-lactone epi-3 was collected.

The ir spectrum (CHCl₃) of (3) had strong carbonyl absorbtion at 1770 cm⁻¹ and an absorbtion at 970 cm⁻¹ for the trans double bond.

In a similar fashion, the other compounds of Example II may be reduced to an epimeric mixture of 3-hydroxy compounds which may be separated by column chromatography.

EXAMPLE IV

2-[5α-Hydroxy-2β-(3α-(tetrahydropyran-2-yloxy)-4-m-tolyloxy-trans-1-buten-1yl)cyclopent-1αyl]acetic acid, γ-lactone (4)

To a solution of 1.5 g. (4.9 mmole) 2-[5α-hydroxy-2β-(3α-hydroxy-4-m-tolyloxy-trans-1-buten-1-yl)cyclopent-1α-yl]acetic acid, γ-lactone (3) in 45 ml. anhydrous methylene chloride and 0.94 ml. of 2,3-dihydropyran at 0° in a dry nitrogen atmosphere was added 15 mg. p-toluenesulfonic acid, monohydrate. After stirring for 30 min., the reaction was diluted with 100 ml. ether and the ether solution washed with saturated sodium bicarbonate (1×15 ml.) then saturated brine (1×25 ml.), dried (Na₂SO₄) and concentrated to yield 2 g. crude 2-[5α-hydroxy-2β-(3α-tetrahydropyran-2-yloxy)-4-m-toloxy-trans-1-buten-1-yl)cyclopent-1α-yl]acetic acid, γ-lactone (4).

The ir (CHCl₃) spectrum had a medium absorbtion at 970 cm³¹ ¹ for the trans double bond and at 1770 cm⁻¹ for the lactone carbonyl.

In a similar fashion, the γ-hydroxy group of the other compounds of Example III may be reacted with 2,3-dihydropyran.

The product of this Example (4) may be catalytically reduced by the procedure of Example XIX to provide the saturated lactone 8 which may be converted by the procedures of Examples V–XVIII and XX–XXI into the 13,14-dihydro two series prostaglandins of this invention.

EXAMPLE V

2-[5α-Hydroxy-2β-(3α-(tetrahydropyran-2-yloxy)-4-m-tolyloxy-trans-1-buten-1-yl)cyclopent-1α-yl]acetaldehyde, γ-hemiacetal (5)

A solution of 2.0 g. (4.95 mmole) 2-[5α-hydroxy-2β-(3α-(tetrahydropyran-2-yloxy)-4-m-tolyloxy-trans-1-buten-1-yl)cyclopent-1α-yl]acetic acid, γ-lactone (4) in 50 ml. dry toluene was cooled to −78° in a dry nitrogen atmosphere. To this cooled solution was added 6.8 ml. of 20% diisobutylaluminium hydride in n-hexane (Alfa Inorganics) dropwise at such a rate that the internal temperature never rose above −65° (20 min.). After an additional 45 min. of stirring at −78°, anhydrous methanol was added until gas evolution ceased and the reaction mixture was allowed to warm to room temperature. The reaction mixture was combined with 100 ml. ether, washed with 50% sodium potassium tartrate solution (4×20 ml) dried (Na$_2$SO$_4$) and concentrated to yield 2.2 g. of crude 2-[5α-hydroxy-2β-(3α-(tetrahydropyran-2-yloxy)-4-m-tolyloxy-trans-1-buten-1-yl)cyclopent-1α-yl]acetaldehyde, γ-hemiacetal (5). Crude 5 was purified by column chromatography on silica gel (Baker "Analyzed"Reagent) eluting with ether and ethyl acetate affording 1.7 g. of pure (5). The product is an epimeric mixture of γ-hemiacetals in which the hydroxy group in the hemiacetal is in either the α- or β-configuration.

In similar fashion, the γ-lactones of Example IV may be converted to γ-hemiacetals.

EXAMPLE VI

9α-Hydroxy-15α-(tetrahydropyran-2-yloxy)-16-m-tolyloxy-cis-5-trans-13-ω-tetranor-prostadienoic acid (10).

To a solution of 2.28 g. (5.16 mmole) (4-carbohydroxy-n-butyl)triphenylphosphonium bromide in 20 ml. of dimethylsulfoxide in a dry nitrogen atmosphere was added 4.25 ml. (9.8 mmole) of a 2.3 m solution of sodium methylsulfinylmethide in dimethyl sulfoxide. To this red ylide solution was added dropwise a solution of 500 mg. (1.29 mmole) 2-[5α- hydroxy-2β-(3α-(tetrahydropyran-2-yloxy)-4-m-tolyloxy-trans-1-buten-1-yl)cyclopent-1α-yl]acetaldehyde, γ-hemiacetal (5) in ml. of dry dimethylsulfoxide over a period of 10 min. After an additional 1 hr. stirring at room temperature, the reaction mixture was poured onto ice water. The basic aqueous solution was washed twice with ethyl acetate (30 ml.) and acidified to pH of about 3 with 10% aqueous hydrochloric acid. The acidic solution was extracted with ethyl acetate (3×40 ml.) and the combined organic extracts washed once with water (20 ml.), dried (Na$_2$SO$_4$) and evaporated to a solid residue. This solid residue was triturated with ethyl acetate and the filtrate concentrated to yield 1.5 g crude 9α-hydroxy-15α-(tetrahydropyran-2-yloxy)-16-m-tolyloxy-cis-5-trans-13-ω-tetranor-prostadienoic acid (10) which was purified by column chromatography using chloroform and ethyl acetate as eluents. After elution of less polar impurities, 388 mg. of pure (10) was collected.

The ir spectrum (CHCl$_3$) displayed a strong band at 1720 cm$^{-1}$ for the carbonyl group.

In similar fashion, (5) may be contacted with [4-(tetrazol-5-yl)-n-butyl] and [4- (N-substituted carboxamide)-n-butyl]triphenylphosphoniumbromide to form the corresponding tetrazole and N-substituted carboxamides.

Also, the other compounds of Example V may be contacted with the above triphenylphosphonium bromides to form the corresponding compounds.

EXAMPLE VII

9-Oxo-15α-(tetrahydropyran-2-yloxy)-16-m-tolyloxy-cis-5-trans-13-ω-tetranor-prostadienoic acid (12)

To a solution cooled to −10° under nitrogen of 388 mg. (0.825 mmole) 9α-hydroxy-15α-(tetrahydropyran-2-yloxy)-16-m-tolyloxy-cis-5-trans-13-tetranor-prostadienoic acid (10) in 25 ml. of reagent grade acetone was added dropwise 0.34 ml. (0.9 mmole) of Jones' reagent. After 3 min. at −10°, 2 drops of 2-propanol was added and the reaction mixture was allowed to stir an additional 5 min. at which time it was combined with 75 ml. ethyl acetate, washed with water (3×20 ml.), dried (Na$_2$SO$_4$) and concentrated to give 400 mg. of crude 9oxo-15α-(tetrahydropyran-2-yloxy)-16-m-tolyloxy-cis-5-trans-13-ω-tetranor-prostadienoic acid (12) which was carried on without further purification.

In similar fashion, the other compounds of Example VI may be converted to the corresponding 9-oxo compounds.

EXAMPLE VIII

9-Oxo-15α-hydroxy-16-m-tolyloxy-cis-5-trans-13-ω-tetranorprostadienoic acid (13)

A solution of 400 mg. (0.95 mmole) crude 9-oxo-15α-(tetrahydropyran-2-yloxy)-16-m-tolyloxy-cis-5-trans-13-ω-tetranorprostadienoic acid (12) in 30 ml. of a 65:35 mixture of glacial acetic acid:water was stirred under nitrogen at 25° for 18 hrs. then concentrated by rotary evaporation. The resultant crude oil was purified by column chromatography on silica gel (Mallinckrodt CC-7 100–200 mesh) using ethyl acetate as eluent. After elution of less polar impurities, the oily 9- oxo-15α-hydroxy-16-m-tolyloxy-cis-5-trans-13-ω-tetranor-prostadienoic acid (13) weighing 97 mg. was collected.

The ir spectrum (CHCl$_3$) displayed carbonyl absorbtion at 1740 cm$^{-1}$ for the ketone, 1710 cm$^{-1}$ for the acid and a band at 970 cm$^{-1}$ for the trans double bond.

In similar fashion, the tetrahydropyran-2-yl group may be removed from the other compounds of Example VII to form the corresponding 15α-hydroxy compounds.

The product prepared above may be reduced by the procedure of Example XX to provide, after purification by column chromatography, the corresponding PGF$_{2\alpha}$ and PGF$_{2\beta}$'s.

EXAMPLE IX

9α,15α-Dihydroxy-16-m-tolyloxy-cis-5-trans-13-ω-tetranorprostadienoic acid (11)

A mixture of 150 mg. (32 mmole) 9α-hydroxy-15α-(tetrahydropyran-2-yloxy)-16-m-tolyloxy-cis-5-trans-13-ω-tetranor-prostadienoic acid (10) in 10 ml. of a 65:35 mixture of glacia acetic acid:water is stirred under nitrogen at 25° for 18 hrs. then concentrated by rotary evaporation. The resultant crude oil is purified by column chromalography on silica gel (Mallinckrodt CC-7 100–200 mesh) using ethyl acetate as eluent. After elution of less polar impurities, the desired 9α,15α-dihydroxy-16-m-tolyloxy-cis-5-trans-13-ω-tetranor-prostadienoic acid (11) is collected.

EXAMPLE X

9Oxo-15α-hydroxy-16-m-tolyloxy-ω-tetranor-prostanoic acid (18)

A mixture of 198 mg. (0.33 mmole) 9-oxo-15α-hydroxy-16-m-tolyloxy-cis-5-trans-13-ω-tetranor-prostadienoic acid (13), 5% palladium on carbon (20 mg.) in methanol (20 ml.) is stirred under an atmosphere of hydrogen for 3 hours at room temperature. The mixture is filtered and concentrated to give the desired 9-oxo-15α-hydroxy-16-m-tolyloxy-ω-tetranor-prostanoic acid (18).

In similar fashion, the other PGE$_2$'s of Example VIII and PGF$_{2\alpha}$'s of Example IX may be reduced to the corresponding PGE$_O$'s and PGF$_{O\alpha}$'s.

Example XI

2-Decarboxy-2-(tetrazol-5-yl)-9α-hydroxy-15α-(tetrahydrofuran-2-yloxy)-16-m-tolyloxy-cis-5-trans-13-ω-tetranorprostadienoic acid (10)

To a solution of 2.42 g. (5.16 mmoles) of 4-(tetrazol-5-yl)-butyltriphenylphosphonium bromide in 20 ml. of dry dimethyl sulfoxide in a dry nitrogen atmosphere was added 4.25 ml. of a 2.2 m solution of sodium methylsulfinylmethide in dimethylsulfoxide. To this red ylide solution was added dropwise a solution of 500 mg. (1.3 mmoles) 2-[5α-hydroxy-2β-(3α-tetrahydropyran-2-yloxy)-4-m-tolyloxy-trans-1-buten-1-yl)cyclopent-1α-yl]acetaldehyde, γ-hemiacetal (5) in 6 ml. of dimethylsulfoxide over a period of 5 min. After an additional 1 hr. stirring at room temperature, the reaction mixture was poured onto ice water. The basic aqueous solution is acidified to pH∼3 and extracted with ethyl acetate (3×75 ml.). The organic extracts were evaporated to a solid residue. This solid residue was triturated with ethyl acetate and the filtrate concentrated to yield 1.5 g. crude 2-descarboxy-2-(tetrazol-5-yl)-9α-hydroxy-15α-(tetrahydropyran-2-yloxy)-16-m-tolyloxy-cis-5-trans-13-ω-tetranorprostadienoic acid (10) which was purified by column chromatography using chloroform and ethel acetate as eluting solvents. After elution of less polar impurities, 450 mg. of pure (10) was collected.

The ir spectrum (CHCl$_3$) displayed absorbtion at 970 cm$^{-1}$ for the trans double bond.

EXAMPLE XII

2-Descarboxy-2-(tetrazol-5-yl)-9-oxo-15α-(tetrahydropyran-2-yloxy)-16-m-tolyloxy-cis-5-trans-13-ω-tetranorprostadienoic acid (12).

To a solution cooled to −10° under nitrogen of 450 mg. (0.905 mmole) 2-descarboxy-2-(tetrazol-5-yl)-9-oxo-15α-(tetrahydropyran-2-yloxy)-16-m-tolyloxy-cis-5-trans-13-ω-tetranorprostadienoic acid (10) in 75 ml. reagent grade acetone was added dropwise 0.37 ml. (1 mmole) of Jones' reagent. After 3 min. at −10°, 3 drops of 2-propanol was added and the reaction mixture was allowed to stir an additional 5 min. at which time it was combined with 125 ml. ethyl acetate, washed with water (3×30 ml.), dried (Na$_2$SO$_4$) and concentrated to give 430 mg. crude 2-descarboxy-2-(tetrazol-5-yl)-9-oxo-15α-(tetrahydropyran-2-yloxy)-16-m-tolyloxy-cis-5-trans-13-ω-tetranorprostadienoic acid (12) which was carried on without further purification.

EXAMPLE XIII

2-Descarboxy-2-(tetrazol-5-yl)-9-oxo-15α-hydroxy-16-m-tolyloxy-cis-5-trans-13-ω-tetranorprostadienoic acid (13)

A solution of 420 mg. (0.85 mmole) crude 2-descarboxy-2-(tetrazol-5-yl)-9-oxo-15α-(tetrahydropyran-2-yloxy)-16-m-tolyloxy-cis-5-trans-13-ω-tetranorprostadienoic acid (12) in 30 ml. of a 65:35 mixture of glacial acetic acid: water was stirred under nitrogen at 25° for 18 hrs. then concentrated by rotary evaporation. The resultant crude oil was purified by column chromatography on silica gel (Mallinckrodt CC-7 100–200 mesh) using ethyl acetate as eluent. After elution of less polar impurities, the oily 2-descarboxy-2-(tetrazol-5-yl)-9-oxo-15α-hydroxy-16-m-tolyloxy-cis-5-trans-13-ω-tetranorprostadienoic acid (13) weighing 206 mg. was collected.

The ir spectrum (CHCl$_3$) displayed a band at 1738 cm$^{-1}$ for the carbonyl absorbtion and at 970 cm$^{-1}$ for the trans double bond.

EXAMPLE XIV

2-Descarboxy-2-(tetrazol-5-yl)-9-oxo-15α-hydroxy-16-m-tolyloxy-ω-tetranorprostanoic acid (18). p A mixture of 205 mg. (0.5 mmoles) 2-descarboxy-2-(tetrazol-5-yl)-9-oxo-15α-hydroxy-cis-5-trans-13-16-m-tolyloxy-ω-tetranorprostadienoic acid (13), 5% palladium on carbon (20 mg.) in methanol (30 ml.) is stirred under an atmosphere of hydrogen for 3 hrs. at room temperature. The mixture is filtered and concentrated to give the desired 2-descarboxy-2-(tetrazol-5-yl)-9-oxo-15α-hydroxy-16-m-tolyloxy-ω-tetranorprostanoic acid (18).

EXAMPLE XV 9,15-Dioxo-16-m-tolyloxy-cis-5-trans-13-ω-tetranorprostadienoic acid (26)

To a solution cooled to −10° under nitrogen of 96 mg. (0.4 mmoles) 9-oxo-15α-hydroxy-16-m-tolyloxy-cis-5-trans-13-ω-tetranorprostadienoic acid (13) in 20 ml. of reagent grade acetone is added dropwise 0.15 ml. (0.4 mmoles) of Jones' reagent. After 3 min. at −10°, 2 drops of 2-propanol is added and the reaction mixture is allowed to stir an additional 5 min. at which time it is combined with 50 ml. of ethyl acetate, washed with water (2×20 ml.), dried (Na$_2$SO$_4$) and concentrated to give the desired 9,15-dioxo-16-m-tolyloxy-cis-5-trans-13-ω-tetranorprostadienoic acid (26).

In a similar manner, the other compounds of Example VIII may be reduced to the corresponding keto compound.

EXAMPLE XVI 9,15-Dioxo-16-m-tolyloxy-ω-tetranorprostanoic acid (32)

A mixture of 100 mg. 9,15-dioxo-16-m-tolyloxy-cis-5-trans-13-ω-tetranorprostadienoic acid (26), 5% palladium on carbon (20 mg.) in methanol (30 ml) is stirred under an atmosphere of hydrogen for 3 hrs. at room temperature. The mixture is filtered and concentrated to give the desired 9,15-dioxo-16-m-tolyloxy-ω-tetranorprostanoic acid (32).

In a similar manner, the compounds of Example XV may be reduced to the corresponding 15-keto PGE$_0$'s.

EXAMPLE XVII

2-Descarboxy-2-(tetrazol-5-yl)-9,15-dioxo-16-m-tolyloxy-cis-5-trans-13-ω-tetranorprostadienoic acid (26)

To a solution cooled to −10° under nitrogen of 102 mg. (0.25 mmoles) 2-descarboxy-2-(tetrazol-5-yl)-9-oxo-15α-hydroxy-16 -m-tolyloxy-cis-5-trans-13-ω-tetranorprostadienoic acid (13) in 30 ml. of reagent grade acetone was added dropwise to 10 ml. (0.28 mmoles) Jones' reagent. After 3 min. at −10°, 1 drop of 2-propanol was added and the reaction mixture allowed to stir an additional 5 min. at which time it was combined with 50 ml. of ethyl acetate, washed with water (2×20 ml.), dried ($Na_2SO_4$) and concentrated to give 100 mg. of crude 2-descarboxy-2-(tetrazol-5-yl)-9,15-dioxo-16-m-tolyloxy-cis-5-trans-13-ω-tetranorprostadienoic acid (26) which was purified by column chromatography on silica gel (Baker "Analyzed" Reagent) eluting with ether to afford 70 mg. of pure (26).

The ir spectrum ($CHCl_3$) displayed absorption at 1740 cm$^{-1}$ for the saturated ketone and at 1700 cm$^{-1}$, 1680 cm$^{-1}$ and 1640 cm$^{-1}$ for the enone.

EXAMPLE XVIII

2-Descarboxy-2-(tetrazol-5-yl)-9,15-dioxo-16-m-tolyloxy-ω-tetranorprostanoic acid (32).

A mixture of 70 mg. 2-descarboxy-2-(tetrazol-5-yl)-9,15-dioxo-16-m-tolyloxy-cis-5-trans-13-ω-tetranorprostadienoic acid (26), 5% palladium on carbon (10 mg.) in methanol (30 ml.) was stirred under an atmosphere of hydrogen for 3 hrs. at room temperature. The mixture was filtered and concentrated to give 68 mg. 2-descarboxy-2-(tetrazol-5-yl)-9,15-dioxo-16-m-tolyloxy-ω-tetranorprostanoic acid (32).

The ir spectrum ($CHCl_3$) had carbonyl absorption at 1740 cm$^{-1}$ for the ketones.

EXAMPLE XIX

2-[5α-hydroxy-2β-(3α-hydroxy-4-tolyloxy-but-1-yl)cyclopent-1α-yl]acaetic acid, γ-lactone (7)

A mixture of 3,4 g (12.5 mmoles) 2-[5α-hydroxy-2β-(3α-hydroxy-4-m-tolyloxy-trans-1-buten-1-yl)cyclopent-1α-yl]acetic acid, γ-lactone (3), 10% palladium on carbon (370 mg.) in 55 ml. of ethyl acetate stirred under an atmosphere of hydrogen for 3 hrs. at room temperature. The mixture was filtered and evaporated to give 2.9 g. 2-[5α-hydroxy-2β-(3α-hydroxy-4-m-tolyloxy-but-1-yl)cyclopent-1α-yl]acetic acid, γ-lactone (7), mp. 60.5°–62.5°.

In a similar fashion, the other compounds of Example III may also be reduced.

The compounds of this Example may be converted to 13,14-dihydro $PGE_2$'s and $PGF_2$'s in the same manner as (2) was converted above into $PGE_2$'s and $PGF_2$'s.

EXAMPLE XX

9-Hydroxy-15α-(tetrahydropyran-2-yloxy)-16-m-tolyloxy-cis-5-trans-13-ω-tetranorprostadienoic acid (15).

To a solution, cooled to −78° of 227 mg. (0.5 mmole) 9-oxo-15α-(tetrahydropyran-2-yloxy)-16-m-tolyloxy-cis-5-trans-13-ω-tetranorprostadienoic acid (12) is added dropwise 1 ml. of a 1.0 M solution of lithium triethylborohydride in tetrahydrofuran. The mixture is stirred for ten minutes then is quenched at −78° by the addition of 1 ml. of a 9:1 mixture of water:acetic acid. The mixture is allowed to warm to room temperature then concentrated. The residue was diluted with ethyl acetate. The organic layer is washed with water and saturated brine, dried ($Na_2SO_4$) and concentrated to afford the desired 9-hydroxy-15α-(tetrahydropyran-2-yloxy)-16-m-tolyloxy-cis-5-trans-13-ω-tetranorprostadienoic acid (15).

In a similar fashion, the other compounds of Example VII may be reduced to the corresponding $PGF_2$'s.

The above prepared product (15) may be hydrolyzed by the procedure of Example VIII to provide the corresponding $PGF_{2\alpha}$ and $PGF_{2\beta}$'s.

EXAMPLE XXI

N-methanesulfonyl 9,15-dioxo-16-(m-tolyloxy)-cis-5-trans-13-ω-tetranorprostadienamide To a solution of 30 mg. of 9,15-dioxo-16-(m-tolyloxy)-cis-5-trans-13-ω-tetranorprostadienoic acid in 5 ml. of dry tetrahydrofuran was added 85 μl. of triethylamine. The solution was stirred for 5 minutes then 80 mg. of N-methanesulfonyl isocyanate was added. The solution was stirred overnight then was neutralized by the addition of acetic acid. Purification of the crude residue by silica gel chromatography using mixtures of ethyl acetate:chloroform as eluents provided the desired N-methanesulfonyl 9,15-dioxo-16-(m-tolyloxy)-cis-5-trans-13-ω-tetranorprostadienamide as a viscous oil weighing 15 mg.

The ir spectrum ($CHCl_3$) exhibited carbonyl absorptions at 1740 cm$^{-1}$ for the ketone, 1715 cm$^{-1}$ for the sulfonimide, and at 1700 cm$^{-1}$ and 1625 cm$^{-1}$ for the enone.

In a similar fashion, any of the above 9,15-dioxo prostaglandin acids may be converted to the corresponding carboxamides.

EXAMPLE XXII (ent)-p-Biphenyl-9-oxo-15α-hydroxy-16-phenoxy-cis-5-trans-13-ω-tetranorprostadienoate To a mixture of 365 mg. (1.02 mmole) of 9-oxo-15α-hydroxy-16-phenoxy-cis-5-trans-13-ω-tetranorprostadienoic acid and 2.07 g. of p-phenylphenol in 40 ml. of dry methylene chloride was added 11.7 ml. of a 0.1 M solution of [1-(3-dimethylaminopropyl)]-3-ethylcarbodiimide in methylene chloride. The mixture was stirred at room temperature for 16 hours under nitrogen then was concentrated. The solid residue was purified by silica gel (Baker "Analyzed" 60–200 mesh) chromatography using mixtures of chloroform:benzene as eluents. After removal of less polar impurities the solid (ent)-p-biphenyl 9-oxo-15α-hydroxy-16-phenoxy-cis-5-trans-13-ω-pentanorprostadienoate was collected weighing 200 mg. and melting at 68°–70°.

EXAMPLE XXIII

2-[5α-Hydroxy-2β-(2,2-dibromovinyl)cyclopent-1α-yl]acetic acid, γ-lactone (41)

To a solution of 138 g (0.528 mole) triphenylphosphine in 800 ml of anhydrous methylene chloride at 0° in a dry nitrogen atmosphere was added in one portion of a solution of 87.3 g (0.264 mole) carbon tetrabromide in 100 ml of anhydrous methylene chloride. The resulting bright orange solution was stirred for 5 minutes. A solution of 20.4 g (0.132 mole) 2-[5α-hydroxy-2β-formyl-cyclopent-1α-yl]acetic acid, γ-lactone (1) in 100 ml of anhydrous methylene chloride was then added over 2 minutes via an addition funnel. After stirring for an additional 4 minutes, the reaction was diluted with 5 liters of pentane and filtered to remove insoluble material. The insoluble fraction was reworked by additional cycles of methylene chloride extraction and pentane precipitation to remove all the olefinic product. The combined pentane fractions were evaporated to yield 90 g (>100%) crude 2-[5α-hydroxy-2β-(2,2-dibromovinyl)cyclopent-1α-yl]acetic acid, γ-lactone (41). The product was purified by chromatography on 700 g of silica gel (Baker "Analyzed" reagent 60–200 mesh). The yield of pure 2-[5α-hydroxy-2β-(2,2-dibromovinyl)cyclopent-1α-yl]acetic acid, γ-lactone (41) was 28.7 g (70%).

The n.m.r. spectrum (CDCl$_3$) exhibited a doublet 6.40δ(1 H) for the vinyl hydrogen, a broad singlet at 5.05δ(1 H) and multiplets at 2.40–3.20δ(4 H) and 1.25–2.40δ(4 H) for the remaining protons. The ir (CHCl$_3$) spectrum had a strong absorption at 1770 cm$^{-1}$ for the γ-lactone carbonyl.

EXAMPLE XXIV

2-[5α-Hydroxy-2β(2,2-dibromovinyl)cyclopent-1α-yl]acetaldehyde, γ-hemiacetal

A solution of 28.7 g (92.6 mmole) 2-[5α-hydroxy-2β-(2,2-dibromovinyl)cyclopent-1α-yl]acetic acid, γ lactone (41) in 700 ml dry toluene was cooled to −78° in a dry nitrogen atmosphere. To this cooled solution was added 114 ml (92.6 mmole) of 20% diisobutylaluminum hydride in n-hexane (Alfa Inorganics) dropwise at such a rate that the internal temperature remained below −66°. After 10 minutes of stirring at −78°, the reaction was diluted with 2.5 liters of ether, washed with 50% sodium potassium tartrate solution (2×200 ml), dried (MgSO$_4$) and concentrated to yield 28.1 g 2-[5α-hydroxy-2β-(2,2-dibromovinyl)cyclopent-1α-yl]acetaldehyde, γ-hemiacetal.

EXAMPLE XXV

2-[5α-Hydroxy-2β-(2,2-dibromovinyl)cyclopent-1α-yl]acetaldehyde, γ-methylacetal

To a solution of 28 g (90 mmole) 2-[5α-hydroxy-2β-(2,2-dibromovinyl)-cyclopent-1α-yl]acetaldehyde, γ-hemiacetal in 500 ml of anhydrous methanol under a dry nitrogen atmosphere at 25° was added 40 drops boron trifluoride etherate. After stirring 25 minutes, the reaction was quenched with 40 ml of saturated aqueous sodium bicarbonate solution. The reaction was evaporated to a volume of 75 ml, diluted with 1 liter of ether. The ether layer was washed with brine (2×100 ml), dried over Na$_2$SO$_4$ and evaporated to yield 30 g (>100%) of crude 2-[5α-hydroxy-2β-(2,2-dibromovinyl)cyclopent-1α-yl]-acetaldehyde, γ-methylacetal.

EXAMPLE XXVI

2-[5α-Hydroxy-2β-ethynyl cyclopent-1α-yl]acetaldehyde, γ-methyl-acetal (42)

A solution of 30.0 g (92 mmole) 2-[5α-hydroxy-2β-(2,2-dibromovinyl)-cyclopent-1α-yl]acetaldehyde, γ-methylacetal in 500 ml of anhydrous tetrahydrofuran was cooled to −78° in a dry nitrogen atmosphere. To this cooled solution was added dropwise 92 ml (202 mmole) of 2.2 M butyl lithium (Alfa Inorganics) at such a rate that the internal temperature remained below −60° (15 minutes). The reaction was stirred for 2 hours at −78° and 1 hour at 25° then quenched with 200 ml ice water and extracted with ether (2×300 ml). The combined ether extracts were washed with brine, dried (Na$_2$SO$_4$) and evaporated to yield 15.8 g crude 2-[5α-hydroxy-2β-ethnyl cyclopent-1α-yl]acetaldehyde, γ-methylacetal (5). The product was purified by distillation yielding 12.9 g (60% from (1)) pure 2-[5α-hydroxy-2β-ethbyl cyclopent-1α-yl]acetaldehyde, γ-methylacetal (42), b.p. 55°–65° at 0.15 mm.

The nmr spectrum (CCl$_4$) exhibited a doublet 4.85 δ (1H) for the acetal proton, a doublet 3.16 δ (3H) for the methoxy protons a multiplet 4.30–4.78 δ (1H) and a multiplet 1.30–3.00 δ (9H) for the remaining protons. The ir (CCl$_4$) spectrum had a strong absorbtion 3320 cm$^{-1}$ for the acetylene.

EXAMPLE XXVII

2-[5α-Hydroxy-2β-(3-hydroxy-4-phenoxy-1-butynyl)-cyclopent-1α-yl]acetaldehyde, γ-methylacetal (43)

A solution of 2.35 g. (14.6 mmole) 2-[5α-hydroxy-2β-ethynylcyclopent-1α-yl]acetaldehyde, γ-methylacetal (42) in 115 ml. of anhydrous tetrahydrofuran was cooled to 0° in a dry nitrogen atmosphere. To this cooled solution was added dropwise (over 10 min.) 10 ml. (22 mmole) 2.2 M n-butyllithiun in n-hexane (Alfa Inorganics). The resulting yellow solution was stirred at 0° for 20 minutes then cooled to −78°. A solution of 2.98 g. (22 mmole) phenoxyacetaldehyde in 10 ml. of anhydrous tetrahydrofuran was then added dropwise at such a rate that the internal temperature remained below −66° (over 10 min.). After stirring for 1 hr. at −78°, the reaction was poured onto water, extracted with ether, dried (Na$_2$SO$_4$) and evaporated to yield 5.8 g. crude 2-[5α-hydroxy-2β-(3-hydroxy-4-phenoxy-1-butynyl)cyclopent-1α-yl]acetaldehyde, γ-methylacetal (43) which was purified by column chromatography on 120 g. silica gel (Baker "Analized" reagent 60–200 mesh). After elution of less polar impurities, 2.4 g. (55%) of product was collected.

The nmr spectrum (CDCl$_3$) exhibited a multiplet at 7.44–6.64 δ (5H) for the phenyl protons, a doublet at 4.93 δ (1H) for the acetal proton, a singlet 3.25 δ (3H) for the methoxy protons and multiplets at 4.81–4.56 δ (2H), 4.20–3.84 δ (2H) and 3.91–1.15 δ (9H) for the remaining protons. The i.r. (CHCl$_3$) spectrum had absorbtion at 3600 cm$^{-1}$ for the hydroxyl.

EXAMPLE XXVIII

Following the method of Example XXVII, a series of 2-[5α-hydroxy-2β-(3-hydroxy-4-aryloxy-1-butynyl)cyclopent-1α-yl]acetaldehydes, γ-methylacetal in which any of the above-mentioned Ar may be the aryl substituent. For instance, Ar may be

| Ar | Ar |
|---|---|
| (p-phenyl)phenyl | (p-bromo)phenyl |
| m-tolyl | (o-chloro)phenyl |
| p-tolyl | (p-ethoxy)phenyl |
| (p-trifluoromethyl)phenyl | (p-fluoro)phenyl |
| α-naphthyl | (p-ethyl)phenyl |
| β-naphthyl | (o-methoxy)phenyl |
| (p-methoxy)phenyl | (m-methoxy)phenyl |
| (o-fluoro)phenyl | (m-fluoro)phenyl |
| (p-chloro)phenyl | (p-isopropyl)phenyl |
| (m-phenyl)phenyl | (p-butyl)phenyl |
| (m-ethyl)phenyl | (m-trifluoromethyl)phenyl |
| (m-bromo)phenyl | (m-chloro)phenyl |
| o-tolyl | (o-bromo)phenyl |

-continued

| Ar | Ar |
|---|---|
| (o-trifluoromethyl)phenyl | (p-isopropoxy)phenyl |

These compounds may be elaborated to prostaglandin analogs in the same manner as the compound of the previous Example.

EXAMPLE XXIX

2-[5α-Hydroxy-2β-(3-benzoyloxy-4-phenoxy-1-butynyl)cyclopent-1α-yl]acetaldehyde, γ-methylacetal (44)

To a solution of 2.4 g. (8 mmole) 2-[5α-hydroxy-2β-(3-hydroxy-2β-(3-hydroxy-4-phenoxy-1-butynyl)cyclopent-1α-yl]acetaldehyde, γ-methylacetal (43) in 24 ml. of anhydrous methylene chloride containing 16 ml. of pyridine was added in one portion 1.67 g. (12 mmole) benzoyl chloride. The reaction was stirred at room temperature in a dry nitrogen atmosphere for 2 hrs., then poured onto water (150 ml.) and extracted with ether (2×300 ml.). The combined ether extracts were washed with cold 10% hydrochloric acid to remove the pyridine. The ether layer was then dried (Na₂SO₄) and evaporated to yield 4.0 g. crude 2-[5α-hydroxy-2β-(3-benzoyloxy-4-phenoxy-1-butynyl)cyclopent-1α-yl]acetaldehyde, γ-methylacetal (44).

EXAMPLE XXX

2-[5α-Hydroxy-2β-(3-benzoyloxy-4-phenoxy-1-butynyl)cyclopent-1α-yl]acetaldehyde, γ-hemiacetal A solution of 4.0 g. crude 2-[5α-hydroxy-2β-(3-benzoyloxy-4-phenoxy-1-butynyl)cyclopent-1α-yl]acetaldehyde, γ-methylacetal (44) in 1 l. of aqueous tetrahydrofuran (50/50 water/tetrahydrofuran) containing 40 drops of concentrated hydrochloric acid was stirred at room temperature during 96 hrs., then extracted with ether (2×500 ml.). The combined ether extracts were evaporated to remove most of the tetrahydrofuran. The residue (100 ml.) was diluted with benzene, dried (Na₂SO₄) and evaporated to yield 3.5 g. crude 2-[5α-hydroxy-2β-(3-benzoyloxy-4-phenoxy-1-butynyl)]acetaldehyde, γ-hemiacetal.

EXAMPLE XXXI

2-[5α-Hydroxy-2β-(3-benzoyloxy-4-phenoxy-1-butynyl)cyclopent-1α-yl]acetic acid, γ-lactone A solution of 3.5 g. (8.95 mmole) crude 2-[5α-hydroxy-2β-(3-benzoyloxy-4-phenoxy-1-butynyl)cyclopent-1α-yl]acetaldehyde, γ-hemiacetal in 150 ml. of acetone was cooled to 0° in a dry nitrogen atmosphere. To this cooled solution was added dropwise (over 5 min.) 3.64 ml. (9.8 mmole) 2.67 M. Jones reagent. After stirring for 45 min. at 0°, the reaction was diluted with water (200 ml.) and extracted with ether (2×300 ml.). The combined ether extracts were dried (Na₂SO₄) and evaporated to yield 3.6 g. crude 2-[5α-hydroxy-2β-(3-benzoyloxy-4-phenoxy-1-butynyl)cyclopent-1α-yl]acetic acid, γ-lactone. The product was purified by column chromatography on 100 g. silica gel (Baker "Analyzed" Reagent 60–200 mesh). The yield of pure 2-[5α-hydroxy-2β-(3-benzoyloxy-4-phenoxy-1-butynyl)cyclopent-1α-yl]acetic acid, γ-lactone was 2.53 g. (81% from (43)).

The n.m.r. spectrum (CDCl₃) exhibited a multiplet at 8.38–7.93 δ (2H) and a multiplet at 7.65–6.77 δ (8H) for the phenyl protons, a triplet at 5.93 δ (1H), a multiplet at 5.08–4.80 δ (1H), a doublet at 4.32 δ (2H) and a multiplet at 3.04–1.56 δ (8H) for the remaining protons. The i.r. spectrum (CHCl₃) had strong absorbtion at 1720 cm⁻¹ and 1770 cm⁻¹ for the ester and lactone, respective.

EXAMPLE XXXII

2-[5α-Hydroxy-2β-(3-hydroxy-4-phenoxy-1-butynyl)-cyclopent-1α-yl]acetic acid, γ-lactone (45)

To a solution of 2.53 g. (6.5 mmole) 2-[5α-hydroxy-2β-(3-benzoyloxy-4-phenoxy-1-butynyl)cyclopent-1α-yl]acetic acid in 50 ml. of anhydrous methanol was added 895 mg. anhydrous powdered potassium carbonate. After stirring at room temperature in a dry nitrogen atmosphere for 2 hrs., the reaction was cooled to 0° and acidified to pH 3 with 1N hydrochloric acid. After stirring for 10 min., the reaction was diluted with water (100 ml.) and extracted with ether (2×150 ml). The combined ether layers was washed with brine, dried (Na₂SO₄) and evaporated to yield 3.6 g. crude 2-[5α-hydroxy-2β-(3-hydroxy-4-phenoxy-1-butynyl)cyclopent-1α-yl]acetic (45). The product was purified by column chromatography on 80 g. of silica gel (Baker "Analyzed" Reagent 60–200 mesh). The yield of pure 2-[5α-hydroxy-2β-(3-hydroxy-4-phenoxy-1-butynyl)cyclopent-1α-yl]acetic acid, γ-lactone (45) was 1.5 g. (81%).

The n.m.r. spectrum (CDCl₃) exhibited a multiplet at 7.54–6.74 δ (5H) for the phenyl protons, a multiplet at 5.04–4.49 δ (2H), a doublet at 4.02 δ (2H), a multiplet at 3.87–3.60 δ (1H) and a multiplet at 2.96–1.50 δ (8H) for the remaining protons. The i.r. spectrum (CHCl₃) had strong absorbtion at 1750 cm⁻¹ for the lactone carbonyl and 3600 cm⁻¹ for the hydroxyl.

EXAMPLE XXXIII

2-[5α-Hydroxy-2β-(3-{tetrahydropyran-2-yloxy}-4-phenoxy-1-butynyl)cyclopent-1α-yl]acetic acid, γ-lactone To a solution of 1.5 g. (5.25 mmole) 2-[5α-hydroxy-2β-(3-hydroxy-4-phenoxy-1-butynyl)cyclopent-1α-yl]acetic acid, γ-lactone (45) in 30 ml. of anhydrous methylene chloride containing 0.72 ml. (7.9 mmole) of 2,3-dihydropyran at 0° in a dry nitrogen atmosphere was added 35 mg p-toluenesulfonic acid, monohydrate. After stirring for 40 min. at 0°, the reaction was poured onto ether (300 ml.). The ether solution as washed with saturated brine (1×25 ml.), dried (Na₂SO₄) and concentrated to yield 1.96 g. crude 2-[5α-hydroxy-2β-(3-{tetrahydropyran-2-yloxy}-4-phenoxy-1-butynyl)cyclopent-1α-yl]acetic acid, γ-lactone.

EXAMPLE XXXIV

2-[5α-Hydroxy-2β-(3-{tetrahydropyran-2-yloxy}-4-phenoxy-1-butynyl)cyclopent-1α-yl]acetaldehyde, γ-hemiacetal A solution of 1.96 g. (5.3 mmole) 2-[5α-hydroxy-2β-(3-{tetrahydropyran-2-yloxy}-4-phenoxy-1-butynyl)cyclopent-1α-yl]acetic acid, γ-lactone in 30 ml. of anhydrous toluene was cooled to −78° in a dry nitrogen atmosphere. To this cooled solution was added 7.4 ml. (5.9 mmole) of 20% diisobutylaluminum hydride in n-hexane (Alfa Inorganics) dropwise at such a rate that the temperature remained below −66° (over 20 min.) After an additional 45 min. of stirring at −78°, the reaction was diluted with ether (300 ml.). The ether solution was washed with 50% sodium potassium tartrate solution (2×100 ml.), dried (MgSO$_4$) and concentrated to yield 3.0 g. crude 2-[5α-hydroxy-2β-(3-{tetrahydropyran-2-yloxy}-4-phenoxy-1-butynyl)cyclopent-1α-yl]acetaldehyde, γ-hemiacetal, which was purified by column chromatography on 120 g. of silica gel (Baker "Analyzed" Reagent). The yield of pure 2-[5α-hydroxy-2β-(3-{tetrahydropyran-2-yloxy}-4-phenoxy-1-butynyl)cyclopent-1α-yl]acetaldehyde, γ-hemiacetal was 1.55 g.

EXAMPLE XXXV

9α-Hydroxy-15-(tetrahydropyran-2-yloxy)-16-phenoxy-ω-tetranorprosta-cis-5-ene-13-ynoic acid (46)

To a solution of 5.55 g. (12.5 mmole) (4-carbohydroxy-n-butyl)triphenylphosphonium bromide in 30 mml. of dry dimethylsulfoxide in a dry nitrogen atmosphere was added 11.7 ml. (23.9 mmole) of a 2.04 M solution of sodium methylsulfinylmethide. To this red ylide solution at 40° (oil bath) was added dropwise a solution of 1.55 g. (4.17 mmole) 2-[5α-hydroxy-2β-(3-[tetrahydropyran-2-yloxy]-4-phenoxy-1-butynyl)cyclopent-1α-yl]acetaldehyde, γ-hemiacetal in 20 ml. of dry dimethylsulfoxide over a period of 5 minutes. After 50 min. at 40°, the reaction was poured onto ice water. The basic aqueous solution (200 ml.) was covered with ethyl acetate (200 ml.) and with vigorous stirring was acidified to pH 3 with 1 N aqueous hydrochloric acid. The acidic solution was extracted with ethyl acetate (2×100 ml.) and the combined organic extracts washed with saturated brine, dried (Na$_2$SO$_4$) and evaporated to a solid residue which was triturated with ether and filtered. The filtrate was concentrated and purified by column chromatography on 120 g. of silica gel (Baker "Analyzed" Reagent 60-200 mesh). After removal of high R$_f$ impurities, 1.26 g. of 9α-hydroxy-15-(tetrahydropyran-2-yloxy)-16-phenoxy-ω-tetranor-prosta-cis-5-ene-13-ynoic acid (46) was collected.

In similar fashion, the product of Example XXXIV may be reacted with the corresponding 4-(tetrazol-5-yl)butyl- and 4-(N-substituted carboxamide-n-butyl)triphenylphosphonium bromides to form the 1-N-substituted carboxamide and 1-(tetrazol-5-yl) analogs of (46).

EXAMPLE XXXVI

9-Oxo-15-(tetrahydropyran-2-yloxy)-16-phenoxy-ω-tetranor-prosta-cis-5-ene-13-ynoic acid To a solution of 850 mg. (1.86 mmole) 9α-hydroxy-15-(tetrahydropyran-2-yloxy)-16-phenoxy-ω-tetranor-prosta-cis-5-ene-13-ynoic acid (46) in 30 ml. of acetone at −10° in a dry nitrogen atmosphere was added 0.75 ml. (2.04 mmole) of 2.67 M Jones Reagent. After 10 min. at −10°, the reaction was poured onto ethyl acetate (350 ml.), washed with water (1×50 ml.), dried Na$_2$SO$_4$) and concentrated to yield 940 mg. crude 9-oxo-15-(tetrahydropyran-2-yloxy)-16-phenyl-ω-tetranor-prosta-cis-5-ene-ynoic acid.

EXAMPLE XXXVII

9-Oxo-15-hydroxy-16-phenoxy-ω-tetranor-cis-5-ene-13-ynoic acid (47)

A solution of 940 mg. of 9-oxo-15-(tetrahydropyran-2-yloxy)-16-phenoxy-ω-tetranor-prosta-cis-5-ene-13-ynoic acid in 25 ml. of a 65:35 mixture of glacial acetic acid:water was stirred under nitrogen at 27° overnight, then concentrated by rotary evaporation. The resultant crude oil was purified by chromatography on 50 silica gel (Mallinckrodt CC-7-100-200 mesh). After elution of less polar impurities the 9-oxo-15-hydroxy-16-phenoxy-ω-tetranor-prosta-cis-5-ene-13-ynoic acid (47) weighing 570 mg. was collected.

The n.m.r. spectrum exhibited a multiplet at 8.00–6.85 δ (7H) for the phenyl, the acid and hydroxyl protons, a broad singlet at 5.50 δ (2H) for the olefinic protons, a triplet at 4.95 δ (1H), a doublet at 4.15 δ (2H) and a multiplet at 3.00–1.10 δ (14H) for the remaining protons. The i.r. spectrum (CHCl$_3$) had strong absorbtion at 1708 cm$^{-1}$ for the carboxylic acid, at 1735 cm$^{-1}$ for the ketone and at 3600 cm$^{-1}$ for the hydroxyl.

EXAMPLE XXXVIII

9α-Hydroxy-15-hydroxy-16-phenoxy-ω-tetranor-cis-5-ene-13-ynoic acid (47)

A solution of 400 mg. of 9α-hydroxy-15-(tetrahydropyran-2-yloxy)-16-phenoxy-ω-tetranor-cis-5-ene-13-ynoic acid (46) in 25 ml. of a 65:35 mixture of glacial acetic acid:water was stirred under nitrogen at 27° overnight, then concentrated by rotary evaporation. The resultant oil was purified by column chromatography on 30 g. of silica gel (Mallinckrodt CC-7100-200 mesh). After elution of less polar impurities the 9α-hydroxy-15-hydroxy-16-phenoxy-ω-tetranor-pros-cis-5-ene-13-ynoic acid (47) weighing 206 mg. was collected.

The n.m.r. spectrum (CDCl$_3$) exhibited a multiplet at 7.60–6.79 δ (5H) for the phenyl protons, a broad singlet at 5.52 δ (5H) for the olefinic, the hydroxyl and the acid protons, a multiplet at 5.00–4.60 (1H), a multiplet at 4.33–3.92 δ (3H) and a multiplet at 2.85–1.11 (14H) for the remaining protons.

EXAMPLE XXXIX

9-Oxo-15α-hydroxy-16-(m-chlorophenoxy)-13-trans-ω-tetranorprostanoic acid

A solution of 58 mg 9-oxo-15α-hydroxy-16-(m-chlorophenoxy)-5-cis-13-trans-ω-tetranorprostadienoic acid in 6 ml of anhydrous ether is treated with 448 mg (3.6 mmole) dimethyl isopropyl chlorosilane and 36.0 mg (3.6 mmoles) triethylamine at 25° for 48 hours. The reaction mixture is cooled to 0°, methanol is added and the resulting solution is washed with water, is dried (anhydrous magnesium sulfate), and is concentrated. The residue is dissolved in methanol (6 ml), 5% palladium in carbon (30 mg) is added, and the resultant slurry is hydrogenated for 4 hours at −22°. After filtration (Celite) and concentration of the filtrate, the product is hydrolyzed in 2 ml of a 65:35 mixture of acetic acid:water for 10 minutes, is diluted with water, and is extracted with ethyl acetate. The combined organic extracts are washed with brine, dried (anhydrous magnesium sulfate), and concentrated to afford 9-oxo-15α-hydroxy-16-(m-chlorophenoxy)-13-trans-ω-tetranor-prostenoic acid (after purification by silica gel chromatography.

EXAMPLE XL

Phenethyl 9α,15α-dihydroxy-16-phenoxy-5-cis-13-trans-ω-tetranorprostadienoate

To a solution of 31 mg of 9α,15α-dihydroxy-16-phenoxy-5-cis-13-trans-ω-tetranorprostadienic acid in 5 ml of ether is added a yellow solution of 1-diazo-2-phenylethane (prepared by oxidation of phenethyl hydrazine) dropwise until the yellow color persists for 5 minutes. Concentration of the solution and silica gel chromatographic purification of the crude residue affords phenethyl 9α,15α-dihydroxy-16-phenoxy-15-cis-13-trans-ω-tetranorprostadienoate.

EXAMPLE XLI

Dodecyl 9-oxo-15α-hydroxy-16-(p-fluorophenoxy)-5-cis-13-trans-ω-tetranorprostadienoate To a solution of 31 mg of 9-oxo-15α-hydroxy-16-(p-fluorophenoxy)-5-cis-13-trans-ω-tetranorprostadienoic acid in 5 ml. of ether is added a yellow solution of diazododecane (prepared by oxidation of dodecyl hydrazine) dropwise until the yellow color persists of 5 minutes. Concentration of the solution and silica gel chromatographic purification of the crude residue affords dodecyl 9-oxo-15α-hydroxy-16-(p-fluorophenoxy)-5-cis-13-trans-ω-tetranorprostadienoate.

EXAMPLE XLII

Methyl 9-oxo-15α-hydroxy-16-(m-trifluoromethyl)-5-cis-13-trans-ω-tetranorprostadienoate To a solution of 75 mg of 9-oxo-15α-hydroxy-16-(m-trifluoromethylphenoxy)-5-cis-13-trans-ω-tetranorprostadienoic acid in 10 ml of ether is added a yellow solution of diazomethane in ether (prepared from N-methyl-N'-nitro-N-nitrosoguanidine) dropwise until the yellow color persists for 5 minutes. Concentration of the solution and silica gel chromatographic purification of the crude residue afford methyl 9-oxo-15α-hydroxy-16-(m-trifluoromethyl)-5-cis-13-trans-ω-tetranorprostadienoate.

EXAMPLE XLIII

Cyclooctyl 9-oxo-15α-hydroxy-16-(β-naphthoxy)-5-cis-3-trans-ω-tetranorprostadienoate To a solution of 130 mg of 9-oxo-15α-hydroxy-16(β-naphthoxy)-5-cis-13-trans-ω-tetranorprostadienoic acid in 7 ml of dry methylene chloride is added 33 mg (0.33 mmole) of triethyl amine. The mixture is stirred for 5 minutes then 36 mg (0.35 mmole) of pivaloyl chloride is added. The solution is stirred for 45 minutes at room temperature under nitrogen then 192 mg (1.5 mmole) of cyclooctyl alcohol and 225µl of pyridine are added. The mixture is stirred at room temperature for an additional 2.0 hours then is diluted with ethyl acetate. The diluted solution is washed with water (2×) and saturated brine (1×), is dried (anhydrous magnesium sulfate), and is concentrated. Purification of the crude residue by silica gel chromatography provides the cyclooctyl 9-oxo-15α-hydroxy-16-(β-naphthoxy)-5-cis-13-trans-ω-tetranorprostadienoate.

What is claimed is:

1. The optically active compounds of the structure

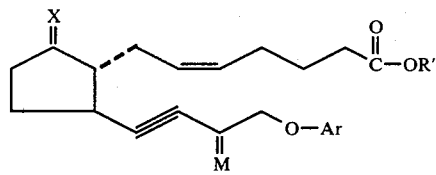

their optical antipodes and the racemates thereof wherein

X and M are selected from the group consisting of keto,

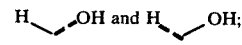

R' is selected from the group consisting of hydrogen, alkyl of from one to ten carbon atoms, aralkyl of from seven to nine carbon atoms, cycloalkyl of from three to eight carbon atoms, α-naphthyl, β-naphthyl, phenyl and monosubstituted phenyl wherein the phenyl substituent is selected from the group consisting of fluoro, chloro, bromo, trifluoromethyl, lower alkyl, lower alkoxy and phenyl; and Ar is selected from the group consisting of phenyl, α-naphthyl, β-naphthyl and monosubstituted phenyl wherein the substituent is selected from the group consisting of fluoro, chloro, bromo, lower alkyl, lower alkoxy, phenyl and trifluoromethyl.

2. A compound according to claim 1 wherein X is keto.

3. A compound according to claim 2 wherein Ar is selected from the group consisting of phenyl, naphthyl and tolyl.

4. A compound according to claim 2 wherein R' is selected from the group consisting of hydrogen and p-biphenyl.

5. A compound according to claim 2 wherein M is

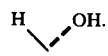

6. A compound according to claim 5 wherein Ar is phenyl and R' is hydrogen.

7. A compound according to claim 1 wherein X is

8. A compound according to claim 8 wherein Ar is selected from the group consisting of phenyl, naphthyl and tolyl.

9. A compound according to claim 8 wherein R' is selected from the group consisting of hydrogen and p-biphenyl.

10. A compound according to claim 8 wherein M is

11. A compound according to claim 11 wherein Ar is phenyl and R' is hydrogen.

12. A compound according to claim 11 wherein Ar is naphthyl and R' is hydrogen.

* * * * *